US012806185B2

(12) United States Patent
Chen et al.

(10) Patent No.: US 12,806,185 B2
(45) Date of Patent: Nov. 24, 2026

(54) USE OF PCSK9 INHIBITOR IN PREPARATION OF PRODUCT FOR TREATING MULTIPLE DISEASES

(71) Applicant: Min Chen, Nanjing (CN)

(72) Inventors: Min Chen, Nanjing (CN); Yichen Wang, Nanjing (CN)

(73) Assignee: Min Chen, Nanjing (CN)

( * ) Notice: Subject to any disclaimer, the term of this patent is extended or adjusted under 35 U.S.C. 154(b) by 846 days.

(21) Appl. No.: 18/024,010

(22) PCT Filed: Jun. 30, 2021

(86) PCT No.: PCT/CN2021/103749

§ 371 (c)(1),
(2) Date: Feb. 28, 2023

(87) PCT Pub. No.: WO2022/002160

PCT Pub. Date: Jan. 6, 2022

(65) Prior Publication Data

US 2023/0346773 A1 Nov. 2, 2023

(30) Foreign Application Priority Data

Jul. 1, 2020 (CN) ......................... 202010623845.1
Jul. 1, 2020 (CN) ......................... 202010623904.5
Oct. 14, 2020 (CN) ......................... 202011093999.0
Nov. 6, 2020 (CN) ......................... 202011228305.X
Mar. 25, 2021 (CN) ......................... 202110321390.2

(51) Int. Cl.

| | |
|---|---|
| *A61K 31/4725* | (2006.01) |
| *A61K 31/4545* | (2006.01) |
| *A61K 31/4965* | (2006.01) |
| *A61K 31/5377* | (2006.01) |
| *A61K 31/713* | (2006.01) |
| *A61K 39/395* | (2006.01) |
| *A61K 45/06* | (2006.01) |
| *A61P 11/00* | (2006.01) |
| *A61P 17/00* | (2006.01) |
| *A61P 17/02* | (2006.01) |
| *C07K 16/40* | (2006.01) |

(52) U.S. Cl.

CPC ........ *A61K 31/4725* (2013.01); *A61K 31/713* (2013.01); *A61K 39/3955* (2013.01); *A61P 11/00* (2018.01); *A61P 17/02* (2018.01)

(58) Field of Classification Search

None
See application file for complete search history.

(56) References Cited

U.S. PATENT DOCUMENTS

2018/0312607 A1* 11/2018 Chen ....................... A61P 17/06

FOREIGN PATENT DOCUMENTS

WO WO-2020160518 A1 * 8/2020 ......... G01N 33/5759

OTHER PUBLICATIONS

Heukels-et-al., https://pubmed.ncbi.nlm.nih.gov/30704705/, 2019.*

* cited by examiner

*Primary Examiner* — Sun Jae Yoo
(74) *Attorney, Agent, or Firm* — JC ONE WORLD

(57) ABSTRACT

Provided in the present invention is the use of a proprotein convertase subtilisin/kexin type 9 (PCSK9) inhibitor in a product for treating multiple diseases. The PCSK9 inhibitor is a PCSK9 small molecule compound, or a PCSK9 interfering RNA, or a PCSK9 monoclonal antibody, or a PCSK9 mimetic peptide, or a PCSK9 mimetic antibody protein, or a PCSK9 antisense oligonucleotide or a PCSK9 vaccine.

7 Claims, No Drawings

Specification includes a Sequence Listing.

SEQUENCE LISTING

```
<160> NUMBER OF SEQ ID NOS: 1

<210> SEQ ID NO 1
<211> LENGTH: 692
<212> TYPE: PRT
<213> ORGANISM: Homo Sapiens
```

-continued

<400> SEQUENCE: 1

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
```

```
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690
```

USE OF PCSK9 INHIBITOR IN PREPARATION OF PRODUCT FOR TREATING MULTIPLE DISEASES

SEQUENCE LISTING

This application contains a Sequence Listing which has been submitted in ASCII format and is hereby incorporated by reference in its entirety. The ASCII copy, is named Sequence_Listing.txt created on Feb. 28, 2023 and is 6,199 bytes in size.

TECHNICAL FIELD

The invention belongs to the field of medical technology, and specifically, it relates to the role of PCSK9 in the treatment of a variety of diseases and the application of PCSK9 inhibitors in the preparation of products for treating various diseases.

BACKGROUND

Vitiligo is a common acquired localized or generalized skin depigmentation disease, with a prevalence of 1% to 2% worldwide. It can occur in all parts of the body, usually in the back of the fingers, wrist, forearm, face, neck, and around the genitals. Etiology includes autoimmune factors, genetic factors, neuropsychiatric factors, and so on. Vitiligo can be associated with autoimmune diseases. Specific antibodies of various organs can be detected in serum, and the immune response may lead to the destruction of melanocytes. Vitiligo is a refractory disease. Systemic treatment is mainly applicable to patients with generalized advanced vitiligo. Oral or intramuscular injection of glucocorticoids can stabilize vitiligo in advanced stage as soon as possible. Topical glucocorticoids are effective for the treatment of localized vitiligo, but long-term use of glucocorticoids can cause many adverse reactions. For the parts that are not suitable for glucocorticoid use, or to avoid adverse reactions caused by long-term use of glucocorticoids, topical calcineurin inhibitors have a certain effect. Narrow-wave ultraviolet (NB-UVB) has some effect on the treatment of localized or generalized vitiligo. Vitamin D3 derivatives can treat vitiligo with NB-UVB, PUVA, etc., or with topical glucocorticoids and calcineurin inhibitors.

Acne, known as youth bean, is a chronic inflammatory disease mainly occurring in the part of hair follicle and sebaceous gland. The incidence rate is about 9.4%, which is common in adolescence. Acne is closely related to the physiological and pathological changes of adolescent skin. The clinical manifestations mainly include acne, papules, pustules, nodules, cysts, scars, etc. The healing time is long, which has a serious impact on the appearance and psychology of patients. Acne is related to multiple pathogenesis. The abnormal keratinization of hair follicle mouth is an important basis of the disease. Inflammation and infection are the pathogenic factors of acne. The sebaceous glands of acne patients are large, the secretion of sebaceous glands is increased, and the level of linoleic acid in sebum is relatively reduced, which affects the synthesis of fat, leading to the lack of fatty acid in follicular epithelium, thus inducing excessive keratinization of follicles, preventing normal shedding of epithelial cells, excessively reducing the sebaceous gland mouth of hair follicles, preventing smooth discharge of sebum, and forming acne. The mouth of the hair follicle sebaceous gland is blocked to form an anoxic environment in the hair follicle sebaceous gland, causing anaerobic propioni bacterium acnes reproduce in large quantities. decompose sebum, produce chemical chemokines, and white blood cells gather to form papules. A large number of neutrophils in the sebaceous glands of hair follicles gather. After neutrophils swallowing propioni bacterium acnes, inflammation occurs, which makes a large number of pus cells accumulate to form pustules and cysts, which are easy to form sunken scars later. When there are nodules and cysts of different sizes on the face, forehead, cheek, jaw, chest, back and shoulder, suppurative infection often occurs. After ulceration, jelly like pus with blood often flows out, and then a sinus is formed.

Diseases with abnormal keratinization mechanisms similar to acne include ichthyosis, keratosis pilaris (also known as lichen pilaris), and porokeratosis. In Keratosis pilaris, follicle openings are enlarged and there is a horn keratotic inside. Ichthyosis manifests as a decrease in sweat and sebaceous glands, and keratinous embolism in hair follicles. The above diseases are likely to recur and are difficult to treat. Clinically, retinoic acid drugs are mainly used to treat abnormal keratosis and eliminate keratin plugs and acne. Retinoic acid drugs can inhibit keratinization, reduce sebum secretion, promote normal keratinization of keratinocytes, and have immune regulation and anti-inflammatory effects, thus reducing the formation of acne, papules, and pustules. They are widely used clinically to treat Dyskeratotic diseases such as acne, ichthyosis, keratosis pilaris, and porokeratosis. However, long term topical use of retinoic acid drugs can lead to skin thinning, photosensitivity and skin barrier damage, while oral use of retinoic acid drugs has adverse reactions such as liver damage and high blood lipid.

On the other hand, acne on the face is very common among people, making the skin look dark, yellow and rough, with large pores, and affecting the beauty. Products that can really solve this problem are very scarce in the market. Therefore, it is necessary to find safe and effective acne control products to meet the needs of Guangda Aimei group.

Alopecia Areata (AA) is a kind of non-scarring alopecia. Alopecia Areata usually presents as sudden patches of hair loss, and in severe cases, it can affect the entire scalp, which is called Alopecia Totalis. When it affects all the hair on the body, including axillary and pubic hair, it is called Alopecia Universalis. It may have a serious impact on the patient's appearance and psychology. Abnormal or unstable autoimmune function and neuropsychiatric factors are considered to be important related factors. The earlier alopecia areata is treated, the higher the chance of cure. Minoxidil can promote the expansion of skin blood vessels, improve local blood circulation, and promote hair growth. It is a common topical drug for the treatment of alopecia areata. For severe alopecia areata, Glucocorticoids including Prednisolone and compound Betamethasone are commonly used as treatment, which can be taken orally, externally, or through intradermal injection. For patients who are not suitable for glucocorticoid drugs, immunosuppressive therapy can be used. which commonly are cyclosporine and methotrexate. Glucocorticoids and immunosuppressants, however, may have many side effects.

Androgenetic alopecia (AGA), also known as seborrheic alopecia (SA), is an androgen-dependent hereditary hair loss. Epidemiological surveys in China show that the prevalence of androgenetic alopecia is 21.3% in males and 6.0% in females. Male hair loss is usually horseshoe shaped. The skin of the hair loss area is bright, and the pores are narrowed or a little soft vellus hair remains. Most women have diffuse hair loss on the top of their heads. The speed, scope and severity of hair loss are affected by genetics and individuals. The etiology and pathogenesis of androgenetic alopecia are still unclear, and it is generally believed that androgens and their receptors play a key role in the occurrence of the disease. Under normal physiological conditions, androgens can stimulate the growth and development of hair in the body, but they can induce hair loss in some specific parts; testosterone is the main androgen in the body. Through 5a-reductase, it is converted into dihydrotestosterone, which can cause the transition from terminal hair to vellus hair, and eventually lead to hair loss. There is currently no ideal treatment for AGA. Systemic and local treatment can refer to other alopecia diseases. Androgenetic alopecia is a refractory type of alopecia, and animal models of the disease are often used as representative models of alopecia. Minoxidil is a non-specific drug for the treatment of hair loss. It is a first-line topical drug approved by the FDA for the treatment of alopecia. However, it may cause facial and limb hirsutism during use. The therapeutic effect would gradually disappear after discontinuation. Finasteride is a type II 5a-selective reductase inhibitor. The FDA has approved oral Finasteride for the treatment of Androgenetic Alopecia, which can continuously improve hair growth. However, Finasteride can cause sexual dysfunction, Oligospermia, Gynecomastia, and other adverse reactions. It has been found to have teratogenic effects in animal experiments, so it is not suitable for children and women of childbearing age. Cimetidine needs to be taken continuously for 5 months or more, and the side effects are male breast development, impotence, and decreased libido, etc. Oral contraceptives: Desoganorgestone, levonorgestrel (levonorgestrel), norgestrel, norgestrel, norgestrel (oxime norgestrel), norgestrel diester and norgestrel acetate are mainly used to treat female with AGA, and their hair will be improved after treatment for 6 to 12 months.

Alopecia caused by antineoplastic drugs is the most common type in the growing period. While eliminating rapidly dividing cancer cells, antineoplastic drugs also attack rapidly dividing cells around the hair follicles to cause hair loss.

The type of Alopecia above is more difficult to treat and easier to repeat. Minodil is a non-specific drug for the treatment of alopecia, and is a first-line topical drug approved by FDA for the treatment of alopecia. However, it may cause facial and limb hirsutism during use, and the treatment effect will gradually disappear after discontinuation. Finasteride is a type II 5a reductase selective inhibitor, which is approved by FDA to treat AGA and can continuously improve hair growth, but it has adverse reactions such as abnormal sexual function, transient reduction of sperm and abnormal development of male breast. Therefore, there is a need to find safer and more effective drugs and products to treat above types of hair loss.

Scar is a symptom that physical, biological, chemical, and other factors cause serious damage to the skin and soft tissue and cannot be self-repaired normally, and thus the repair is replaced by fibrous tissue. It will not only affect the appearance but also affect the function. It is difficult to treat scars. At present, we can only make the red and hard scars soft and shallow, the wide scars narrow, and the thick scars thin, but not completely eliminate the scars. It is therefore important to start intervention at the early stage of wound healing, which can effectively reduce the formation of scars, improve the appearance, correct the deformity and restore function. At present, the commonly used methods to treat scars include surgical treatment, laser treatment, cryotherapy, and drug treatment. Commonly used drugs are glucocorticoids and retinoic acid. Glucocorticoids have obvious anti-fibrosis effects, but long-term use of glucocorticoids has many side effects. Retinoic acid is an intermediate product of vitamin A metabolism in the body, which can reduce local inflammation, promote the growth of epithelial cells, reduce collagen synthesis, reduce the DNA synthesis of fibroblasts, and inhibit cell growth. The higher the concentration of retinoic acid drugs, the more obvious the inhibition of growth. However, the curative effect of retinoic acid is limited, and there are many toxic and side effects of systematic application. External use has obvious skin irritation, which increases with the increase of concentration.

Pulmonary fibrosis is a diffuse lung disease with unknown etiology and complex pathogenesis. It is the result of excessive deposition of the extracellular matrix due to excessive repair after lung injury. Repeated damage and excessive repair of alveolar epithelium is the key to the pathogenesis. The pathological features are long-term chronic pulmonary inflammation and persistent alveolar damage leading to the accumulation of extracellular matrix metalloproteinases (MMPs), especially the abnormal increase of MMP-2 and MMP-9, and the decrease of tissue inhibitor of metalloproteinase-1 (TIMP-1), leading to the accumulation of a large number of extracellular matrix, tissue cell remodeling and excessive collagen deposition in the lung. At the same time, it inhibits the expression of vascular endothelial growth factor (VEGF) in tissues, reduces the permeability of pulmonary venules, inhibits the division and proliferation of vascular endothelial cells and angiogenesis, aggravates lung tissue damage, and eventually leads to diffuse interstitial lung disease—pulmonary fibrosis. At present, there is no effective anti-fibrotic drug, and glucocorticoids are commonly used in clinical practice to reduce the anti-fibrosis process, but the efficacy is limited and there are many adverse reactions.

For the problems above, the current treatment methods are far from meeting the demand More new drugs with good efficacy, few side effects, and low prices are needed to control the disease progression, reduce recurrence and complications, and reduce mortality.

Proprotein convertase Subtilisin/Kexin type 9 (PCSK9) is a member of the protein convertase family, which is secreted as an inactive zymogen in the liver. The size of the PCSK9 gene cDNA is 3617bp, encoding PCSK9 protein composed of 692 amino acids. The PCSK9 precursor undergoes intramolecular autocatalytic separation of its N-terminal propeptide within the endoplasmic reticulum. The separated N-terminal propeptide is linked to the catalytic region, allowing mature PCSK9 protein to leave the endoplasmic reticulum and enter the secretory pathway. After PCSK9 is secreted out of the cell, it binds to the low-density lipoprotein (LDL) receptor in the first epidermal growth factor-like region on the cell surface, and the PCSK9-LDL receptor complex can enter the lysosome for degradation, resulting in the decrease of LDL receptor on the cell surface, which means that, PCSK9 levels were negatively correlated with LDL receptors. Many studies have shown that the loss of PCSK9 gene mutation function can significantly reduce the LDL-C level and the incidence of coronary heart disease in different races. Given the significant effect of inhibiting PCSK9 on reducing the incidence of LDL-C and coronary heart disease, multiple treatment schemes are under development to block PCSK9 drugs to reduce the incidence of LDL-C and coronary heart disease.

PCSK9 inhibitors include two categories: 1. Block the binding of PCSK9 to LDL-R, such as monoclonal antibodies, peptidomimetics (polypeptide inhibitors), and antibody protein-mimicking drugs; 2. Inhibit the expression of PCSK9 molecules or interfere with PCSK9 secretion, such as small molecular RNA interference, antisense oligonucleotides, small molecule compound inhibitors, etc. Monoclonal antibodies have become the focus of new drug research due to their high blocking efficiency, accuracy, and good stability. At present, PCSK9-targeted monoclonal antibodies on the global market are all drugs that prevent the binding of PCSK9 to LDL-R, including Evolocumab jointly developed by Amgen and Astellas with trade name Repatha, Alirocumab jointly developed by Sanofi and Regeneron with the trade name Praluent, and Eli Lilly company's LY3015014, JunshiPharma's anti-PCSK9 monoclonal antibody JS002, and Salubris (Xinlitai) Pharmaceutical's Anti-PCSK9, and monoclonal Antibody InjectionSAL003. Clinical studies have found that the above drugs are well tolerated in the treatment of hypercholesterolemia, and there is no significant difference in the incidence of adverse reactions between the placebo group and the active treatment group. In addition, Inclisiran is a siRNA (small interfering RNA) drug, which is different from the monoclonal antibody that directly binds to PCSK9 molecules. It can inhibit the expression of the PCSK9 gene, so that the LDL receptor will not be degraded by PCSK9, thus improving hepatocytes' uptake of LDL particles, and reducing LDL levels in the blood. Alnylam's Inclisiran uses proprietary technology to combine lipid nanoparticles with GalNAc (N-acetylgalactosamine), and GalNAc can combine with the sialogly coprotein receptors ASGR1 and ASGR2 expressed on the surface of liver cells. This technology allows subcutaneous administration and targeting of drugs to the liver. Alnylam has now transferred Inclisiran to Novartis Pharmaceuticals. Affiris company's ALN-PCS and ALN-PCSsc are also siRNA (small interfering RNA) drugs. PCSK9 small interfering RNA inhibitor drugs also include ALN-PCS and ALN-PCSsc from Affiris. What's more, Pfizer has designed a related vaccine drug, and Affiris has designed ATO4A and ATO6A vaccines, for which patients only need to receive the vaccine once a year to achieve long-term LDL-lowering effects, thus reducing the frequency of use. PCSK9 mimetic peptide and PCSK9 mimetic antibody protein drugs include DS9001 from Pieris and 1G08 from Merck. PCSK9 antisense oligonucleotide drugs include SPC5001 of Santaris Pharma, etc.

So far, there is no relevant literature, expertise, or products on the application of PCSK9 inhibitors in the treatment of vitiligo, alopecia, scar, pulmonary fibrosis, as well as in the treatment of acne, ichthyosis, keratosis pilaris, and dyskeratotic diseases.

SUMMARY

The problem to be solved in the invention was: to clarify the role of the PCSK9 gene in the pathogenesis of vitiligo, alopecia, scar, pulmonary fibrosis, and skin diseases of keratinization abnormalities such as acne, ichthyosis, keratosis pilaris, and porokeratosis, and the application of PCSK9 inhibitors in the preparation of products for the treatment of the above diseases. The invention discovered the key role of PCSK9 in vitiligo, alopecia, abnormal keratosis, scar, pulmonary fibrosis, mechanism, and the application of PCSK9 inhibitors in the preparation of products for treating the above diseases through the animal and cell model experimental study of related diseases.

The invention found the important role of PCSK9 gene in promoting skin pigmentation by establishing a representative vitiligo animal model of depigmentation disease.

The PCSK9 protein sequence is shown in sequence 1 in the sequence list.

By establishing the rabbit ear acne model, the invention found that PCSK9 gene plays a key role in the pathogenesis of acne and the application value of PCSK9 inhibitor in the preparation of acne treatment products. The pathogenesis of abnormal keratosis, such as ichthyosis, peridermal keratosis, follicular keratosis and porokeratosis, is characterized by the appearance of angular emboli similar to acne, and the expansion of hair follicle mouth. Since there is no mature animal research model of abnormal keratosis such as ichthyosis, peridermal keratosis, follicular keratosis and porokeratosis, this study selected the rabbit ear acne model as a representative to study the role of PCSK9 in the pathogenesis of the above abnormal keratosis, and the role of PCSK9 inhibitor in improving skin keratosis and inhibiting the formation of angle plugs.

Androgen alopecia is a refractory type of alopecia disease. The animal model of this disease is usually used as the representative model of alopecia disease. By establishing an androgenic alopecia animal model, the invention found that PCSK9 gene plays a key role in the pathogenesis of alopecia disease and the application value of PCSK9 inhibitor in the preparation of drugs for the treatment of alopecia disease.

By establishing a rat skin scar model, the invention found that PCSK9 gene plays a key role in the formation mechanism of scar and the application value of PCSK9 inhibitor in the preparation of products for preventing and treating scar.

The role of PCSK9 gene in the pathogenesis of pulmonary fibrosis and the application of PCSK9 inhibitor in the preparation of products for the treatment of pulmonary fibrosis were clarified by establishing a rat pulmonary fibrosis model.

Technical Solutions of the Invention

The C57BL/6 mouse is an animal model widely used at home and abroad to study the hair cycle: the hair cycle of each human hair follicle is not synchronized, but this mouse can show unique hair cycle synchronization, so it is often used as a hair research model. Melanocytes of the mouse's trunk skin only exist in hair follicles, and melanin is synthesized only during the growth phase. During the growth period of hair, melanocytes in the hair bulb continuously produce melanin and transmit it to the hair follicle keratinocytes, making the skin appear black; during the degenerative phase, the production of melanin is reduced and the skin is grayish black; In the resting phase, the hair follicles stop producing melanin due to the shrinkage of the hair bulb, and the skin turns pink. The hair in the rest period, after being plucked, can be locally induced into a highly synchronous new hair cycle, which is histologically consistent with the natural cycle of the mouse. Changes in the hair cycle can therefore be inferred from changes in skin color. The invention adopted subcutaneous injection of testosterone propionate injection to create an experimental androgenetic alopecia model and found that PCSK9 gene knockout can significantly promote the hair growth of androgenetic alopecia model mice, and reduce the damage to subcutaneous hair follicles and sebaceous glands. The invention used paraffin wax depilation to establish a non-specific hair loss model in mice, and it proved that the PCSK9 inhibitor has a very obvious promoting effect on hair growth. The invention, through the androgenetic alopecia model experiment, also found that the hair growth rate in the PCSK9 inhibitor group was significantly higher than that of the model control group, which confirmed the effect of the PCSK9 inhibitor in treating alopecia. The experiment confirmed that systemic or topical PCSK9 inhibitors can significantly promote hair growth.

Rabbit ear is an animal model commonly used to measure the effect of acne-causing substances, and the size of sebaceous glands in rabbits varies greatly like humans. With the increase of age, the ability of animals to form acne also increases. Therefore, adult male rabbits are selected to replicate the acne model, so that the male glucocorticoids in the body have a certain stimulating effect on the skin. Adapalene can remove keratin plugs by regulating the abnormal keratinization process of pilosebaceous epithelium, so as to prevent and eliminate acne lesions. Therefore, in this study, adapalene (trade name: Daphne) was selected as the positive control of the experiment. Among the inhibitors that can obviously block PCSK9, the invention respectively selected representative PCSK9 monoclonal antibodies, PCS K9 polypeptide inhibitors, PCSK9 small molecule compound inhibitors, and PCSK9 small interfering RNA to treat rabbit ear acne models by subcutaneous injection or skin external application. The results showed that the symptoms of the PCSK9 inhibitor group were significantly lighter than those of the model control group. The experiment confirmed that systemic or topical PCSK9 inhibitors can significantly inhibit the symptoms of rabbit ear acne models, and reduce the formation of hair follicle keratotic plugs and blackheads, which showed that PCSK9 inhibitors have a therapeutic effect on acne.

The invention applies 2% coal tar solution on the inner side of the ear of New Zealand rabbits, once a day, for 14 days continuously, to establish a acne micro-pigmentation model, observe the thickness, hardness, roughness of the ear and whether there is black angle plug at the hair follicle mouth and other local skin changes with naked eyes, and conduct histological grading and scoring of experimental acne under the microscope. Through the above research, PCSK9 gene knockout can significantly inhibit the symptoms of the rabbit acne model induced by coal tar, reduce pore clogging, and significantly inhibit the formation of blackhead acne, confirming that PCSK9 plays a key role in the pathogenesis of acne.

Among the inhibitors that can significantly block PCSK9, the representative PCSK9 monoclonal antibody, PCSK9 polypeptide inhibitor, PCSK9 small molecule compound inhibitor and PCSK9 small interfering RNA were selected to treat the rabbit ear acne model by subcutaneous injection or external skin application, and compared with the negative control group and the positive drug (Dufuren). The results showed that the symptoms of the PCSK9 inhibitor group were significantly lighter than those of the model control group, and no local and systemic adverse reactions, such as erythema, edema, desquamation, etc., occurred in each PCSK9 inhibitor group. The rabbits' activities and foraging were normal, and no respiratory and central nervous system abnormalities were found. Experiments have proved that both systemic and topical PCSK9 inhibitors can significantly inhibit the symptoms of rabbit ear acne model, reduce the formation of hair follicle angle plug and blackhead acne, and have mild and no irritation to the skin, indicating that PCSK9 inhibitors have obvious therapeutic effect on acne.

Through research, the invention found that PSCK9 gene knockout can significantly promote the healing of skin wounds, reduce scar formation, and also can clearly inhibit the proliferation of skin fibroblasts and promote fibroblast apoptosis in mice model. It showed that PSCK9 can inhibit the proliferation of skin fibroblasts and promotes their apoptosis to inhibit the formation of scars. Among the inhibitors (blockers) that can obviously block PCSK9. The invention selected representative PCSK9 monoclonal antibodies, PCSK9 polypeptide inhibitors, PCSK9 small molecule compound inhibitors, and PCSK9 small interfering RNA, respectively, and intervened in mouse scar models by tail vein injection or skin external application. It was found that PCSK9 inhibitors with higher concentrations can reduce scar formation.

The invention established a pulmonary fibrosis model by tracheotomy and injecting bleomycin into a mouse's neck trachea. Studies found that PSCK9 gene knockout can significantly increase the levels of MMP-2, MMP-9, and VEGF in the lung tissue of a mouse model of pulmonary fibrosis, reduce the level of TIMP-1, and at the same time increase the levels of SOD and CAT enzymes in peripheral blood, showing that it has an inhibitory effect on pulmonary fibrosis. Among the inhibitors that can obviously block PCSK9, the invention respectively selected representative PCSK9 monoclonal antibodies, PCSK9 polypeptide inhibitors, PCSK9 small molecule compound inhibitors, and PCSK9 small interfering RNA inhibitors to treat pulmonary fibrosis. The experiment confirmed that PCSK9 inhibitors can significantly improve the laboratory indicators of pulmonary fibrosis, indicating that PCSK9 inhibitors have therapeutic effects on pulmonary fibrosis.

In the above animal experiments, there were no systemic adverse reactions in each PCSK9 inhibitor group, the animal activity and foraging were normal, and no respiratory and central nervous system abnormalities were found.

Based on the mechanism of action of PCSK9 mentioned above, it is well known to those skilled in the art that PCSK9 inhibitors have therapeutic effects on other similar diseases. PCSK9 inhibitors can be used alone or in combination with other drugs or treatments.

Based on the above research, the invention included the application of PCSK9 inhibitors (blockers) in the preparation of products for the treatment of vitiligo, dyskeratotic diseases, alopecia, scars, pulmonary fibrosis. Wherein the PCSK9 belongs to the proprotein convertase family (gene bank serial number: 255738); the abnormal keratosis diseases include acne, ichthyosis, keratosis pilaris, keratosis follicles, and porokeratosis, etc.; the alopecia diseases include androgenetic alopecia or alopecia areata or alopecia caused by anti-tumor therapy.

The PCSK9 inhibitor described in the invention can be any conventional product or method that can inhibit the expression or secretion of the PCSK9 gene by molecular biology or medicinal chemistry, such as but not limited to, knocking out the or silencing PCSK9 gene through existing molecular biology techniques. In some embodiments, the preferably selected PCSK9 inhibitors can also be employed. The PCSK9 inhibitor (blocker) mentioned above can be PCSK9 small molecule compound or PCSK9 RNA interference or PCSK9 monoclonal antibody or PCSK9 mimetic peptide or PCSK9 mimetic antibody protein or PCSK9 antisense oligonucleotide or PCSK9 vaccine.

In some examples, the PCSK9 small molecule compounds described in the invention include but are not limited to R-IMPPa product of Selleck Company, chemical formula: C24H27N3O2, molecular weight: 389.49, structural formula:

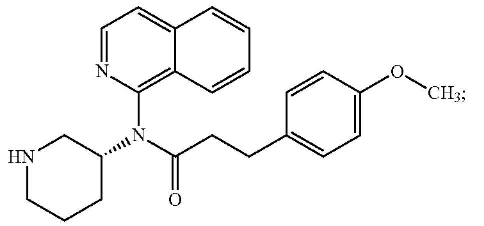 [SMILES: COc1ccc(CCC(=O)N(c2nccc3ccccc23)[C@@H]2CCCNC2)cc1]

Or Selleck company product PF 06446846, chemical formula: C22H20ClN7O, molecular weight: 433.04, structural formula:

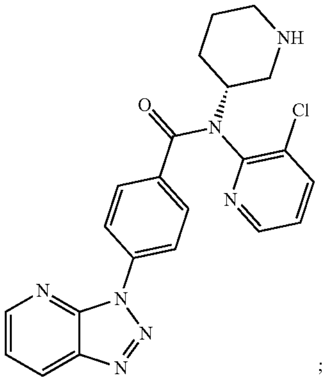 [SMILES: O=C(c1ccc(-n2nnc3cccnc32)cc1)N(c1ncccc1Cl)[C@@H]1CCCNC1]

;

Or Selleck company product SBC-115076, chemical formula: C31H33N3O5, molecular weight: 527.61, structural formula:

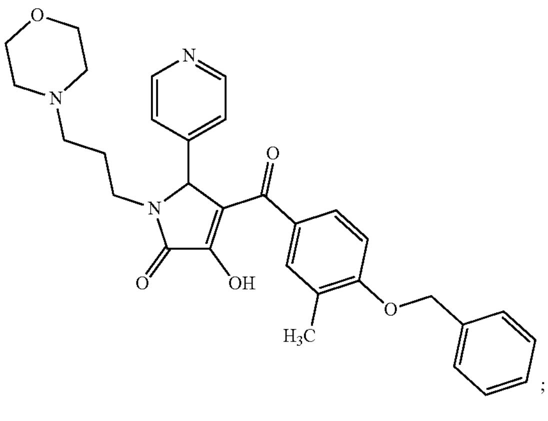 [SMILES: Cc1cc(C(=O)C2=C(O)C(=O)N(CCCN3CCOCC3)C2c2ccncc2)ccc1OCc1ccccc1]

;

Or Selleck company product SBC-110736, chemical formula: C26H27N3O2, molecular weight: 413.51, structural formula:

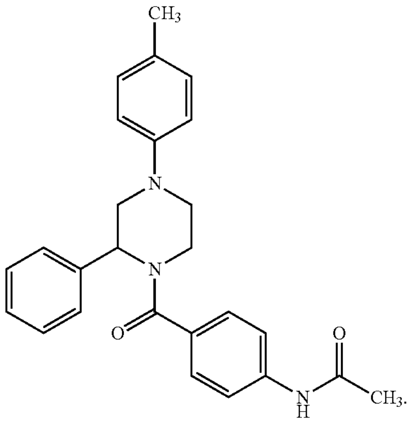 [SMILES: CC(=O)Nc1ccc(C(=O)N2CCN(c3ccc(C)cc3)CC2c2ccccc2)cc1]

In some examples, the PCSK9 monoclonal antibody inhibitors described in the invention include, but are not limited to, ab84041 from Abcam, Evolocumab jointly developed by Amgen and Astellas, Alirocumab jointly developed by Sanofi and Regeneron, the anti-PCSK9 monoclonal antibody JS002 of Junshi Bio, Salubris (Xinlitai) Pharmaceutical's anti-PCSK9 aonoclonal antibody injection SAL003, Eli Lilly's LY3015014, or Merck. Pharmaceutical's 1G08.

In some examples, the PCSK9 RNAi inhibitors described in the invention include, but are not limited to, Inclisran from Alnylam and ALN-PCS and ALN-PCSsc from Affiris Company.

In some examples, the PCSK9 analog peptide inhibitors and PCSK9 analog antibody protein inhibitors described in the invention include but are not limited to DS9001 of Pieris Company and 1G08 of Merck Company.

In some examples, PCSK9 antisense oligonucleotide inhibitors described in the invention include, but are not limited to, SPC5001 from Santaris Pharma Company.

In some examples, the PCSK9 vaccine inhibitors described in the invention include, but are not limited to, ATO4A and ATO6A from Affiris Company.

PCSK9 inhibitors (blockers) can be used alone or in combination with other drugs or treatments.

The invention also provides a pharmaceutical composition, which uses the compound or a pharmaceutically acceptable salt as an active ingredient or main component.

The compounds or compositions of the invention can be prepared in any pharmaceutically acceptable dosage form, such as the preparation suitable for topical skin, oral, parenteral, intraperitoneal, intravenous, intra-arterial, transdermal, sublingual, intramuscular, rectal, buccal, intranasal, inhalation, vaginal, intraocular, subcutaneous, intra-articular, intraperitoneal or any intrathecal forms.

In a preferred embodiment, the dosage form of the invention are solution, tincture, spirit, liniment, spray, emulsion, ointment, gel, patch, water, tablet, granule, oral liquid tablets, capsules, drop pills, enema, film or injection.

The beneficial effects compared with prior art: The invention provides new and better treatment methods for vitiligo, dyskeratotic diseases, alopecia, scars, pulmonary fibrosis. Through the disclosure of the invention, PCSK9 inhibitor (blocker) products can be further prepared. The new monomer drugs or compound preparations containing various PCSK9 inhibitors can be developed for the treatment of the above diseases. Existing clinical experiments have proved that such drugs containing PCSK9 inhibitors have significant curative efficacy, smaller adverse reactions, and good tolerance in the treatment of the above diseases. Even when used externally alone, it can significantly improve symptoms, which is very suitable for clinical needs. It can provide a series of new products with lower prices, good curative effects, and safety for the market.

DETAILED DESCRIPTION

The embodiments of the invention are described below through specific examples, and those skilled in the art can easily understand other advantages and effects of the invention from the contents disclosed in this description. The invention can also be implemented or applied through different specific embodiments, and various details in this specification can also be modified or changed based on different viewpoints and applications without departing from the spirit of the invention.

Before further describing the specific embodiments of the invention, it should be understood that the protection scope of the invention is not limited to the following specific embodiments; it should also be understood that the terms used in the examples are intended to describe specific embodiments, not to limit the scope of protection of the invention; in the specification and claims of the invention, the singular forms "a", "an" and "this" include the plural forms unless the context clearly dictates otherwise.

When numerical ranges are given in the examples, it is to be understood that, unless otherwise indicated herein, both endpoints of each numerical range and any value between the two endpoints can be selected. Unless otherwise defined, all technical and scientific terms used in the invention have the same meaning as commonly understood by medical professionals. In addition to the specific methods, equipment, and materials used in the embodiments, according to the mastery of the invention by skilled medical professionals and the description of the invention, the previously established methods, equipment, and materials similar or equivalent to those described in the embodiments of the present invention can also be used to realize the present invention, which shall fall belongs to the protection scope of the invention.

Example 1 Effect of PCSK9 Gene Knockout on Pigment Growth in Mice

1. Method 1.1 Experimental Animals:

SPF C57BL/6 (B6) mice, C57BL/6-PCSK9−/− mice (using CRISPR gene editing technology to knock out Pcsk9 gene exon 2-3, and establish a Pcsk9 gene knockout mouse model), body weight (20 ±4.6) g.

1.2 Animal Grouping and Modeling

Mice of different genotypes were divided into three groups: C57BL/6 mouse blank control group, C57BL/6 mouse model group, and C57BL/6-PCSK9−/− mouse model group, with 6 mice in each group, 3 males and 3 females. The black hair in the area of 2cm×2cm on the back was removed. Except for the blank control group, in other groups 5% hydroquinone was applied to the hair removal area for decolorization, 0.5 mL each time, twice a day, and the animals in the blank control group were smeared with the same amount of normal saline every day. After 30 days of continuous smearing, if obvious white spots appear in the model group, they indicate that the model was successful. After modeling, the pigmentation of the decolorized part where 5% hydroquinone is applied was observed.

1.3 Observation Indexes and Test Methods 1.3.1 Histological Observation

After the observation, the mice were sacrificed, and the skin tissue on the back about 1 cm×1 cm where 5% hydroquinone was smeared was cut for histopathological examination. 1.3.2 1 Melanocyte (MC) Count in Vitiligo Animal Model The excised mouse skin tissue was fixed in 10% formalin for 1 hour, washed with running water for 3-4 min, and placed into a phosphate buffer solution (pH 7.4) containing 0.1% dihydroxyphenylalanine, and let stand at 37° C. for 1 hour. Then it was replaced with fresh Dopa reagent and left at 37° C. for 12 hours, rinsed with running water, and fixed with Bouin's solution continuously for 24 h. After the specimens were taken out, it was rinsed with running water for 4 hours, dehydrated, cleared in xylene, embedded in paraffin, deparaffinized to water, and stained with hematoxylin-eosin for contrast. Dehydrated and routinely mounted. After Dopa-oxidase staining, brown-black staining was MC positive. The number of MCs in each group was measured under a high-power light microscope, 10 high-power fields were observed for each sample, and the average number of MCs in each 100 epidermal basal cells was calculated.

1.3.3 Count of Melanin-granule-containing Basal Cells in Epidermis of Vitiligo Mouse Model The excised mouse skin tissue was fixed in 10% formalin, dehydrated, cleared with xylene, embedded in paraffin, sectioned, deparaffinized to water, washed with distilled water several times, then stained with Lillie reagent, soaked with ferric chloride and potassium ferricyanide mixed solution for 15-20 minutes, then differentiated with 1% acetic acid aqueous solution for several minutes, washed with distilled water several times, then quickly dehydrated with 95% ethanol and absolute ethanol, cleared in xylene, and sealed with neutral gum. After Lillie reagent staining, if melanin was dark green, it was positive. The number of basal cells containing melanin granules in each group was determined under the light microscope, 10 high-power fields were observed for each specimen, and the average number of basal cells containing melanin granules in every 100 epidermal basal cells was calculated.

1.3.4 Inspection of Tyrosinase Activity in Skin Tissue of Vitiligo Mouse Model

The excised mouse skin tissue was fixed in 10% formalin dehydrated, cleared in xylene, embedded in paraffin, sectioned, deparaffinized to water, then 50 μL of peroxidase blocking agent (3% H2O2) was added to each section for 10 min to block endogenous peroxidase activity. The sections were immersed in 0.01 mol·L-1 PBS buffer and microwaved for 10 min, added with 50 μL mouse anti-human tyrosinase monoclonal antibody, left at 37° C. for 60 min, then added with 50 μL of Elivision reagent, left at 37° C. for 30 min. The sections were then placed in freshly prepared DAB-H2O2 chromogenic solution for color development, rinsed with distilled water, stained with hematoxylin for contrast for 1 min, and sealed with neutral gum. The tyrosinase-positive product was located in the cytoplasm of the cell, shown as yellow or brownish-yellow granules or clumps in the cells under the microscope. The two-level scoring method was used to determine the results. If the number of positive cells was less than 5%, the score was 0; 5%~25% is 1 point; 2 points for 25%~50%; 3 points for 50%~75%; >75% is 4 points. When classified according to staining intensity: 1 point for light yellow; 2 points for yellow or dark yellow; 3 points for brown or brownish yellow. If the sum of the two was less than 2, it was negative (−); 2-3 points as positive (+); 4-5 points as moderately positive (2+); 6-7 points as strongly positive (3+).

1.4 Statistical Methods

The experimental data were statistically processed by SPSS 16.0 system software. Statistical variables of experimental data were expressed as (x±s), using x2 test and t-test, and the Wilcoxon rank sum test was used to compare the intensity of tyrosinase in animal skin tissue. The a value was taken on both sides, where P>0.05 indicated no significant difference, P<0.05 indicated a significant difference, and P<0.01 indicated a highly significant difference.

2. Results 2.1 The Effect of Various PCSK9 Inhibitors on the Counts of Epidermal MC and Melanin-granule-containing Basal Cells in the Vitiligo Guinea Pig Model Caused by Hydroquinone bleaching.

After hydroquinone bleaching, compared with the C57BL/6-PCSK9−/− mouse model group, the content of epidermal MC in the skin tissue of the C57BL/6 mouse model group decreased (P<0.01), and the count of basal cells containing melanin granules decreased (P<0.01). See Table 1

TABLE 1

The counts of MC and basal cells containing melanin granules in the epidermis of mice in each group (n = 6, x ± s)

| Group | Epidermal melanocyte count | Melanocyte-granule-containing basal cell count |
|---|---|---|
| Blank control group | 35.6 ± 2.2* | 38.7 ± 2.1* |
| C57BL/6-PCSK9-/-mouse model group | 28.5 ± 2.8* | 33.5 ± 3.2* |
| C57BL/6mouse model group | 12.7 ± 1.3 | 17.3 ± 2.6 |

Note:
*Compared with C57BL/6 mouse model group, P < 0.01

2.2 Effect of PCSK9 Gene Knockout on Tyrosinase Intensity in Skin Tissue of Vitiligo Mouse Model Induced by Hydroquinone Depigmentation After hydroquinone depigmentation, the tyrosinase intensity in the skin tissue of the C57BL/6 mouse model group was significantly lower than that of the blank control group (P<0.01). Compared with the C57BL/6 mouse model group, the C57BL/6-PCSK9−/− mouse model group could increase the intensity of tyrosinase in the skin tissue of the vitiligo mouse model group (P<0.01). See Table 2

TABLE 2

Tyrosinase intensity of mouse skin tissue caused by hydroquinone and the depigmentation in each group (n = 6)

| Group | Positive cells number (units) | Color (units) | number (units) | Intensity |
|---|---|---|---|---|
| Blank control group | 50% (3) | Brownish-yellow (2) | 5 | +++* |
| C57BL/6-PCSK9-/-mouse model group | 33.3% (2) | Brownish-yellow (2) | 4 | +++* |
| C57BL/6mouse model group | 16.7% (1) | Yellow (1) | 2 | + |

Note:
*Compared with C57BL/6 mouse model group, P < 0.01

3. Conclusion

PCSK9 gene knockout can increase the number of epidermal MC and melanin-granule-containing basal cells in the skin tissue of vitiligo model, and improve the tyrosinase intensity of skin tissue.

Example 2 The Effect of PCSK9 Inhibitor on Pigment Growth in Mice

1. Methods 1.1 Materials (1) PCSK9 RNA-1 interference sequence and modification are shown in table 3.

TABLE 3

| Genes | 5'-3' Sense | 5'-3' Antisense |
|---|---|---|
| siPCSK9-1 | GccuGGAGuuuAuucGGAAdT*dT | UUCCgAAuAAACUCcAGGCdT*dT |
| siPCSK9-2 | AGGuGuAucuccuAGAcAcdT*dT | GUGUCuAGGAGAuAcACCUdT*dT |

Mix equal amounts of siPcsk9-1 and 2 and dilute them to 20 μM with normal saline, and mix the diluted siRNA evenly with the lotion.

PCSK9 RNAi inhibitor-2: RNA sequence is the same as Alnylam's Inclisran; PCSK9RNAi inhibitor-3: RNA sequence is the same as Affiris' ALN-PCS.

(2) PCSK9 small molecule compound inhibitor 1: R-IMPP from Selleck company, chemical formula: C24H27N3O2, molecular weight: 389.49, structural formula:

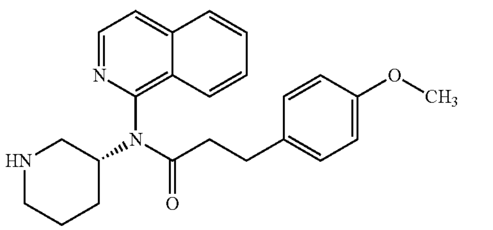 [SMILES: COc1ccc(CCC(=O)N(c2nccc3ccccc23)[C@@H]2CCCNC2)cc1]

PCSK9 small molecule compound inhibitor 2: PF 06446846 from Selleck company, chemical formula: C22H20ClN7O, molecular weight: 434.04, structural formula:

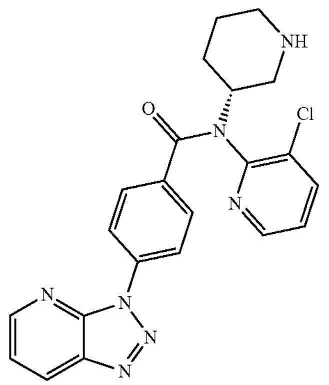 [SMILES: O=C(c1ccc(-n2nnc3cccnc32)cc1)N(c1ncccc1Cl)[C@@H]1CCCNC1]

PCSK9 small molecule compound inhibitor 3: Selleck company product SBC-115076, chemical formula: C31H33N3O5, molecular weight: 527.61, structural formula:

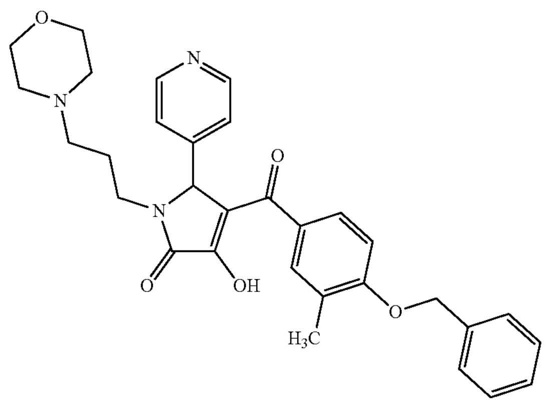 [SMILES: Cc1cc(C(=O)C2=C(O)C(=O)N(CCCN3CCOCC3)C2c2ccncc2)ccc1OCc1ccccc1]

PCSK9 small molecule compound inhibitor 4: Selleck company product SBC-110736, chemical formula: C26H27N3O2, molecular weight: 413.51, structural formula:

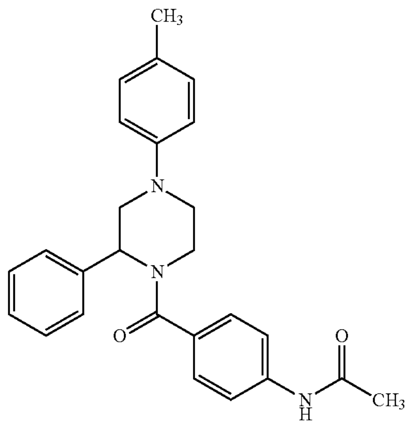 [SMILES: CC(=O)Nc1ccc(C(=O)N2CCN(c3ccc(C)cc3)CC2c2ccccc2)cc1]

(3) PCSK9 monoclonal antibody 1: purchased from Abcam company (ab84041); PCSK9 monoclonal antibody 2: Evolocumab; PCSK9 monoclonal antibody 3: Alirocumab.

(4) PCSK9 polypeptide-11 is ab32727 of Abcam Company.

(5) Positive control drug: mometasone furoate cream (trade name: Eloson, produced by Schering-Plough China Co., Ltd.)

(6) Experimental animal SPF black guinea pig, body weight (252±18) g, half male and half female.

(7) Preparation method of treatment cream: The excipient matrix components include methyl silicone oil (15%), stearic acid (6%), white vaseline (5%), liquid paraffin (5%), octadecanol (5%), glycerin (20%), alkyl aryl polyglycol ether (1%), fatty alcohol polyoxyethylene ether (1%), tween-807 (1%), ethyl paraben (0.1%), distilled water (about 31-55%), and mixed with more than appropriate amount of PCSK9 inhibitors to form a mixed emulsion. The cream matrix used in this embodiment refers to the matrix component from which the active ingredient is removed from the cream.

1.2 Animal Grouping and Modeling

SPF black guinea pigs with a body weight of (252±18) g were selected and numbered according to the body weight, and were randomly divided into compound group 1 (skin applied with 0.1% R-IMPP cream) and compound group 2 (skin applied with 0.1% PF 06446846 cream), compound group 3 (skin applied with 0.1% SBC-115076 cream), compound group 4 (skin applied with 0.1% SBC-110736 cream), monoclonal antibody group 1 (subcutaneous injection of PCSK9 monoclonal antibody ab81041, 1 mg/kg·d), monoclonal antibody group 2 (subcutaneous injection of Evolocumab, 1 mg/kg·d), monoclonal antibody group 3 (subcutaneous injection of Alirocumab, 1 mg/kg·d), PCSK9 RNA interference group-1 (skin applied with 0.1% PCS K9 Small RNA-1 interference cream), PCSK9 RNA interferencegroup-2 (skin applied with 0.1% PCSK9 small RNA-2 interference cream), PCSK9 interference RNA group-3 (skin applied with 0.1% PCSK9 small RNA-3 interference cream), positive treatment group (skin applied with Eloson), blank control group (skin applied with Vaseline), and the model control group (skin applied with Vaseline). 10 in each group, Half male and female. Except for the blank control group, the other groups were smeared with 5% hydroquinone in the hair removal area for decolorization, 0.5 mL each time, twice a day, and the animals in the blank control group were smeared with an equal amount of normal saline every day. After 30 days of continuous smearing, obvious white spots appeared, indicating that the model was successful. After modeling, the drug was administered in the above manner, once a day for 30 days.

1.3 Observation Indexes and Test Methods 1 3 1 Immunohistochemistry

After the observation, the mice were sacrificed, and the skin tissue on the back about 3 cm×3 cm was cut for histopathological examination.

1.3.2 Epidermal Melanocyte (MC) Count in Vitiligo Animal Model

The excised mouse skin tissue was fixed in 10% formalin for 1 hour, washed with running water for 3-4 min, and placed into a phosphate buffer solution (pH 7.4) containing 0.1% dihydroxyphenylalanine, and let stand at 37° C. for 1 hour. Then it was replaced with fresh Dopa reagent and left at 37° C. for 12 hours, rinsed with running water, and fixed with Bouin's solution continuously for 24 h. After the specimens were taken out, it was rinsed with running water for 4 hours, dehydrated, cleared in xylene, embedded in paraffin, deparaffinized to water, and stained with hematoxylin-eosin for contrast. Dehydrated and routinely mounted. After Dopa-oxidase staining, brownish-black staining was MC positive. The number of MCs in each group was measured under a high-power light microscope, 10 high-power fields were observed for each sample, and the average number of MCs in each 100 epidermal basal cells was calculated.

1.3.3 Count of Melanin-granule-containing Basal Cells in the Epidermis of Vitiligo Mouse Model The excised mouse skin tissue was fixed in 10% formalin, dehydrated, cleared with xylene, embedded in paraffin, sectioned, deparaffinized to water, washed with distilled water several times, then stained with Lillie reagent, soaked with ferric chloride and potassium ferricyanide mixed solution for 15-20 minutes, then differentiated with 1% acetic acid aqueous solution for several minutes, washed with distilled water several times, then quickly dehydrated with 95% ethanol and absolute ethanol, cleared in xylene, and sealed with neutral gum. If melanin was dark green after Lillie reagent staining, it was positive. The number of basal cells containing melanin granules in each group was determined under the light microscope, 10 high-power fields were observed for each specimen, and the average number of basal cells containing melanin granules in every 100 epidermal basal cells was calculated.

1.3.4 Inspection of Tyrosinase Activity in Skin Tissue of Vitiligo Mouse Model

The excised mouse skin tissue was fixed in 10% formalin dehydrated, cleared in xylene, embedded in paraffin, sectioned, deparaffinized to water, then 50 μL of peroxidase blocking agent (3% H2O2) was added to each section for 10 min to block endogenous peroxidase activity. The sections were immersed in 0.01 mol·L-1PBS buffer and microwaved for 10 min, added with 50 μL mouse anti-human tyrosinase monoclonal antibody, left at 37° C. for 60 min, then added with 50 μL of Elivision reagent, left at 37° C. for 30 min. The sections were then placed in freshly prepared DAB-H2O2 chromogenic solution for color development, rinsed with distilled water, stained with hematoxylin for contrast for 1 min, and sealed with neutral gum. The tyrosinase-positive product was located in the cytoplasm of the cell, shown as yellow or brownish-yellow granules or clumps in the cells under the microscope. The two-level scoring method was used to determine the results. If the number of positive cells was less than 5%, the score was 0; 5%~25% is 1 point; 2 points for 25%~50%; 3 points for 50%~75%; >75% is 4 points. When classified according to staining intensity: 1 point for light yellow; 2 points for yellow or dark yellow; 3 points for brown or brownish yellow. If the sum of the two was less than 2, it was negative (−); 2-3 points as positive (+); 4-5 points as moderately positive (2+); 6-7 points as strongly positive (3+).

1.4 Statistical Methods

The experimental data were statistically processed by SPSS 16.0 system software. Statistical variables of experimental data were expressed as (x±s), using x2 test and t test, and Wilcoxon rank sum test was used to compare the intensity of tyrosinase in animal skin tissue. The a value was taken on both sides, where P>0.05 indicated no significant difference, P<0.05 indicated a significant difference, and P<0.01 indicated a highly significant difference.

2. Results 2.1 The Effect of Various PCSK9 Inhibitors on the Counts of Epidermal MC and Melanin-granule-containing Basal Cells in the Vitiligo Guinea Pig Model Caused by Hydroquinone bleaching.

After hydroquinone depigmentation, compared with the blank control group, the content of MC in the epidermis of guinea pigs in the model group decreased (P<0.01), and the count of basal cells containing melanin granules decreased (P<0.01). After PCSK9 inhibitors acted on the vitiligo guinea pig model caused by hydroquinone depigmentation in each group, the PCSK9 inhibitor in administration groups could increase the epidermal MC count in the skin tissue of the vitiligo model animals (P<0.01); each PCSK9 inhibitor group could increase the number of melanin-containing basal cells in skin tissue of vitiligo guinea pigs (P<0.01). See Table 4.

TABLE 4

The effect of each group on the counts of guinea pig epidermis MC and melanin-granule-containing basal cells caused by hydroquinone decolorization (n = 10, x ± s)

| Group | Epidermal melanocyte count | Basal cells containing melanin granules count |
|---|---|---|
| model control group | 15.2 ± 2.1 | 21.6 ± 1.8 |
| Blank control group | 43.5 ± 2.3* | 42.8 ± 3.2* |
| Positive treatment group | 42.6 ± 2.1* | 41.2 ± 2.9* |
| Monoclonal antibody group 1 | 35.6 ± 3.3* | 38.5 ± 4.3* |
| Monoclonal antibody group 2 | 46.2 ± 3.8* | 41.2 ± 3.9* |
| Monoclonal antibody group 3 | 43.5 ± 3.6* | 39.6 ± 3.7* |
| Compound group 1 | 33.6 ± 2.9* | 36.5 ± 3.8* |
| Compound group 2 | 39.3 ± 3.2* | 38.8 ± 3.9* |
| Compound group 3 | 36.1 ± 2.8* | 36.9 ± 3.6* |
| Compound group 4 | 34.6 ± 2.6* | 36.8 ± 3.7* |
| RNA interference group 1 | 31.8 ± 2.6* | 33.2 ± 2.9* |
| RNAinterference group 2 | 32.6 ± 2.8* | 36.1 ± 3.2* |
| RNA interference group 3 | 33.8 ± 2.7* | 35.3 ± 3.1* |
| Peptide group | 29.7 ± 3.5* | 32.4 ± 3.6* |

Note:
*Compared with the model control group, P < 0.01

2.2 Effects of Various PCSK9 Inhibitors on Tyrosinase Intensity in Skin Tissue of Vitiligo Guinea Pig Model Induced by Hydroquinone Depigmentation After hydroquinone depigmentation, the tyrosinase intensity in the skin tissue of guinea pigs in the model group was significantly lower than that in the blank control group (P<0.01). After various PCSK9 inhibitors were applied to the vitiligo guinea pig model caused by hydroquinone depigmentation, various PCSK9 inhibitor groups all could increase the intensity of tyrosinase in the skin tissue of the vitiligo guinea pig model animal (P<0.01). See Table 5

TABLE 5

The effect of each group on the tyrosinase intensity of guinea pig skin tissue caused hydroquinone depigmentation (n = 10)

| Group | Number of positive cells (units) | Color (units) | Total number (units) | Intensity |
|---|---|---|---|---|
| Model control group | 10% (1) | Yellow (1) | 2 | + |
| Blank control group | 40% (4) | Brownish-yellow (3) | 7 | +++* |
| Positive treatment group | 30% (3) | Brownish-yellow (3) | 6 | +++* |
| Monoclonal antibody group 1 | 30% (3) | Brownish-yellow (3) | 6 | +++* |
| Monoclonal antibody group 2 | 40% (4) | Brownish-yellow (4) | 7 | +++* |
| Monoclonal antibody group 3 | 30% (3) | Brownish-yellow (4) | 7 | +++* |
| Compound group 1 | 30% (3) | Brownish-yellow (2) | 5 | +++* |
| Compound group 2 | 40% (4) | Brownish-yellow (3) | 7 | +++* |
| Compound group 3 | 30% (3) | Brownish-yellow (3) | 6 | +++* |
| Compound group 4 | 30% (3) | Brownish-yellow (3) | 6 | +++* |
| RNA interference group1 | 20% (2) | Yellow (2) | 4 | ++* |
| RNA interference2 | 30% (3) | Yellow (2) | 5 | +++* |
| RNA interference3 | 30% (3) | Yellow (2) | 5 | +++* |
| Peptide group | 20% (2) | Yellow (2) | 4 | ++* |

Note:
*Compared with the model control group, $P < 0.01$

3. Conclusions

Various PCSK9 inhibitors can treat depigmentation diseases by increasing the number of epidermal MCs and melanin-granule-containing basal cells in skin tissue of the vitiligo model, and improving skin tissue tyrosinase intensity Example 3 Effect of PCSK9 Gene Knockout on Rabbit Ear Acne Model 1. Method 1.1 Animal Grouping and Modeling Experimental animals: SPF New Zealand rabbits, PCSK9−/− SPF New Zealand rabbits (using CRISPR gene editing technology to knock out the Pcsk9 gene exon 2-3 to establish a Pcsk9 gene knockout rabbit model), 1.8-2.3 kg, male. Animals come from southern mold organisms.

Grouping and modeling: rabbits of different genotypes were divided into three groups: negative control group, model control group, and PCSK9−/− model group, with 6 rabbits in each group. The inside of the right ear of the rabbit was treated as the observation area after depilation. The negative control group was coated with 95% alcohol. The model control group and the PCSK9−/− model group were coated with 2% coal tar solution (Alfa Aesar China). 2% coal tar solution was made with 95% alcohol, and was evenly applied to the opening of the ear canal on the inner side of the rabbit ear with a sterile cotton swab in a range of about 2 cm×2 cm, once a day, 0.5 mL each time. The previous application site was wiped with warm water for 14 consecutive days to establish acne micro acne model. The changes in the local skin, the thickness, hardness, roughness of the ears, and the presence or absence of black keratotic plugs at the mouth of the hair follicles were observed with the naked eye. 18 hours after the last application, the samples were sacrificed, and the skin tissue was obtained by punching a 5 mm hole punch at the application site, fixed in 10% formaldehyde, embedded in paraffin, and stained with HE for histopathological analysis.

1.2 Observation Indicators

Histological grading standard of the acne model: 3 grades, according to histology. Grade 0 means that there are only loose keratinized cells in the infundibulum, without acne forming the "1"; grade 1: the skin on the surface of the rabbit ear is red, or a small amount of dense keratinized material is seen in the infundibulum of the hair follicle, and the infundibulum is not expanded "+";grade 2: moderately dense keratinized material is seen in the infundibulum of the hair follicle, and it extends to the sebaceous glands, with the proliferation of sebaceous gland ducts, the infundibulum expands by "2+"; grade 3: extensive keratinized material in the hair follicle. Tight keratin embolism in hair follicles causes severe expansion of hair follicles, obvious hyperplasia of sebaceous duct epithelium, skin bulges and scars, and some sebaceous glands degenerate into "3+".

2. Results

After 14 days of coal tar application, the rabbit ears of the negative control group were soft, thin, and white, the capillaries were clear, and the pores at the openings of the ear canal were uniform in size. In the model control group, the ear thickness of rabbits increased and became hard. The hair follicles had black keratotic plugs, which were similar to papules, and the hair follicles were raised and pimple-like. The surface was rough and dry, and some of them were fused into pieces. The skin of the external auditory canal of the rabbits in the PCSK9−/− model group was slightly rough and dry, and the pores were slightly enlarged. There was no black substance blocking the pores and no papules were observed by the naked eyes.

Observation of tissue sections: Compared with the negative control group, the rabbit ears of the model control group showed different degrees of hypertrophy of granular layer and acanthus, keratinization of the hair follicle orifice, and destruction of the skin tissue structure. In the PCSK9−/− model group, only slight thickening of skin spinous layer and slight increase of hair follicle area were seen. The histological grades of experimental acne in each group are shown in Table 6.

TABLE 6

| Histological grading of acne in each group | | | | | |
|---|---|---|---|---|---|
| Group | n | − | 1+ | 2+ | 3+ |
| Negative control group | 10 | 10 | 0 | 0 | 0 |
| Model control group | 10 | 0 | 1 | 4 | 5 |
| PCSK9-/-Model group | 10 | 8 | 2 | 0 | 0 |

It can be seen from Table 6 that the model group that knocks out Pcsk9 gene can effectively reduce the incidence rate of acne micro acne. It can also be seen that inhibiting Pcsk9 gene can indeed achieve similar effects.

3. Conclusion

PCSK9 gene knockout can significantly inhibit the symptoms of coal-tar-induced acne rabbit model, reduce pore blockage, and significantly reduce the formation of blackheads.

Example 4 Effect of PCSK9 Inhibitor on Rabbit Ear Acne Model

1. Experimental Method:

1.1 Materials (1) PCSK9 RNA-1 interference sequence and modification are shown in table 7.

TABLE 7

| Genes | 5'-3' Sense | 5'-3' Antisense |
|---|---|---|
| siPCSK9-1 | GccuGGAGuuuAuucGGAAdT*dT | UUCCgAAuAAACUCcAGGCdT*dT |
| siPCSK9-2 | AGGuGuAucuccuAGAcAcdT*dT | GUGUCuAGGAGAuAcACCUdT*dT |

Mix equal amounts of siPcsk9-1 and 2 and dilute them to 20 μM with normal saline, and mix the diluted siRNA evenly with the lotion.

PCSK9 RNAi inhibitor-2: RNA sequence is the same as Alnylam's Inclisran; PCSK9RNAi inhibitor-3: RNA sequence is the same as Affiris' ALN-PCS.

(2) PCSK9 small molecule compound inhibitor 1: R-IMPP from Selleck, chemical formula: C24H27N3O2, molecular weight: 389.49, structural formula:

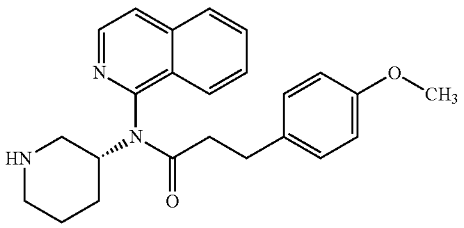 [SMILES: COc1ccc(CCC(=O)N(c2nccc3ccccc23)[C@@H]2CCCNC2)cc1]

PCSK9 small molecule compound inhibitor 2: PF 06446846 from Selleck, chemical formula: C22H20ClN7O, molecular weight: 434.04, structural formula:

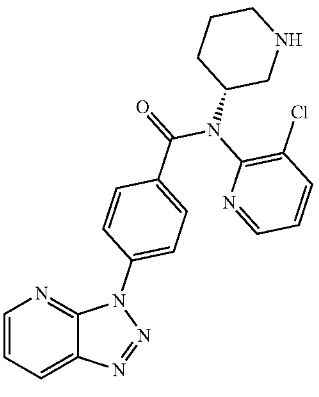 [SMILES: O=C(c1ccc(-n2nnc3cccnc32)cc1)N(c1ncccc1Cl)[C@@H]1CCCNC1]

PCSK9 small molecule compound inhibitor 3: Selleck company product SBC-115076, chemical formula: C31H33N3O5, molecular weight: 527.61, structural formula:

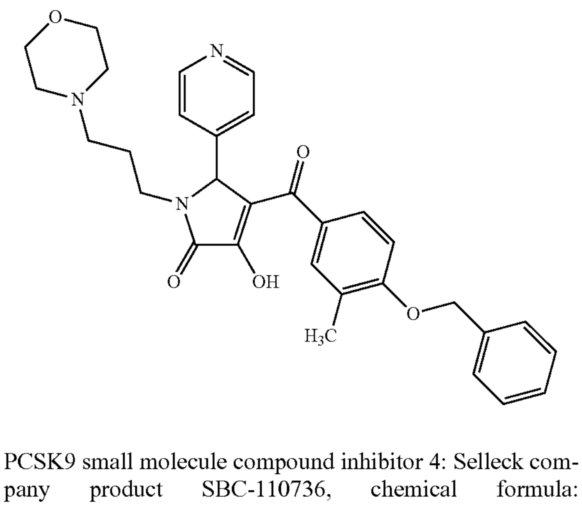

PCSK9 small molecule compound inhibitor 4: Selleck company product SBC-110736, chemical formula: C26H27N3O2, molecular weight: 413.51, structural formula:

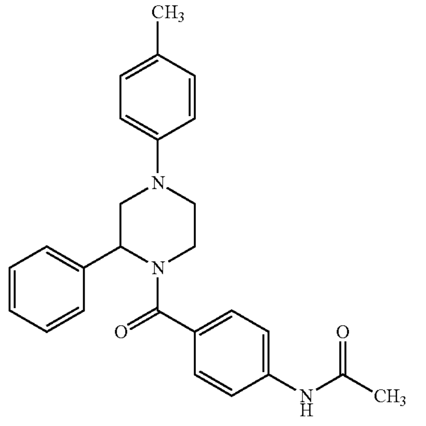 [SMILES: CC(=O)Nc1ccc(C(=O)N2CCN(c3ccc(C)cc3)CC2c2ccccc2)cc1]

(3) PCSK9 monoclonal antibody 1: purchased from Abcam company (ab84041); PCSK9 monoclonal antibody 2: Evolocumab; PCSK9 monoclonal antibody 3: Alirocumab.

(4) PCSK9 polypeptide-11: ab32727 of Abcam Company.

(5) Positive treatment drug: 0.1% adapalene gel (trade name: Differin, produced by Galderma, France)

(6) Experimental animals Ordinary New Zealand rabbits, 1.9-2.4 kg, male, from Shanghai Slac Laboratory Animal Co., Ltd.

Preparation method of treatment cream: The excipient matrix components include methyl silicone oil (15%), stearic acid (6%), white vaseline (5%), liquid paraffin (5%), octadecanol (5%), glycerin (20%), alkyl aryl polyglycol ether (1%), fatty alcohol polyoxyethylene ether (1%), tween-807 (1%), ethyl paraben (0.1%), distilled water (about 31-55%), and mixed with more than appropriate amount of PCSK9 inhibitors to form a mixed emulsion.

The cream matrix used in this embodiment refers to the matrix component from which the active ingredient is removed from the cream.

1.2 Animal Grouping and Modeling

According to body weight, they were randomly divided into compound group 1 (skin applied with 0.1% R-IMPP cream), compound group 2 (skin applied with 0.1% PF 06446846 cream), compound group 3 (skin applied with 0.1% SBC-115076 cream), compound group 4 (skin applied with 0.1% SBC-110736 cream), PCSK9 RNA interference-group-1 (skin applied with 0.1% PCSK9 small RNA-1 cream), PCSK9 RNA interference group-2 (skin applied with 0.1% Inclisran cream, twice a day), PCSK9 RNA interference group-3 (skin applied with 0.1% ALN-PCS cream), monoclonal antibody group 1 (subcutaneous injection of PCSK9 monoclonal antibody ab81041, 1 mg/kg·d), monoclonal antibody group 2 (subcutaneous injection of Evolocumab, 1 mg/kg·d), monoclonal antibody group 3 (subcutaneous injection of Alirocumab, 1 mg/kg·d), Peptide group (subcutaneous injection of Abcam company ab32727, 0.5 mg/kg·d), combination therapy Group 1 (skin applied with 0.1% PF 06446846 cream and 0.1% adapalene gel), combination therapy group 2 (skin applied with 0.1% PCSK9 small interfering RNA-1 cream and 0.1% adapalene gel), positive treatment group (skin applied with 0.1% adapalene gel), model control group (skin applied with cream base), external application twice a day, subcutaneous injection once a week, 10 mice in each group. The inner side of the right ear of the rabbits was taken as the observation area, the left ear of all rabbits was used as the self-negative control, and 95% alcohol was applied. The inner side of the right ear of the model group and the treatment group were smeared with 2% coal tar (Alfa Aesar China Company, 2% coal tar solution made with 95% alcohol), and evenly applied to the opening of the ear canal on the inner side of the rabbit ear with a sterile cotton swab in a range of about 2 cm×2 cm, once a day, 0.5 mL each time. Then the previous application was wiped with warm water. After 14 days of continuous application to establish an acne microcomedone model, the changes in the local skin were observed with the naked eye, including the ear thickness, hardness, roughness, and the presence or absence of black keratotic plugs at the hair follicle opening. 18 hours after the last coating, the samples were sacrificed, fixed in 10% formaldehyde, embedded in paraffin, and stained with HE for histopathological analysis.

1.3 Observation Indicators

Histological grading standard of the acne model: 3 grades, according to histology. Grade 0 means that there are only loose keratinized cells in the infundibulum, without acne forming the "1"; grade 1: the skin on the surface of the rabbit ear is red, or a small amount of dense keratinized material is seen in the infundibulum of the hair follicle, and the infundibulum is not expanded "+"; grade 2: moderately dense keratinized material is seen in the infundibulum of the hair follicle, and it extends to the sebaceous glands, with the proliferation of sebaceous gland ducts, the infundibulum expands by "2+"; grade 3: extensive keratinized material in the hair follicle. Tight keratin embolism in hair follicles causes severe expansion of hair follicles, obvious hyperplasia of sebaceous duct epithelium, skin bulges and scars, and some sebaceous glands degenerate into "3+".

Histopathological changes were observed under a microscope, and the thickness of 5 different epidermises on a slice was measured with the Biomias99 image analysis system, and the average value was calculated; the area of two hair follicles with the same position and the most complete structure and the diameter of four sebaceous glands were detected, and the average value of each was calculated, and then the data of the left and right external auditory canals of each group were subtracted to obtain the difference in the thickness of the epidermis, the difference in hair follicle area and the diameter of the sebaceous gland in the left and right ears of each rabbit.

1.4 Statistical Processing

Statistical analysis was performed with SPSS16 software. Paired t-test was used for the left and right controls, and the t-test was used for comparison between groups. $P<0.05$ as the difference was statistically significant.

2. Results

Visual observation: After 14 days of coal tar coating, the skin of the left ear of the rabbits in all groups was soft, the hair follicles of the external auditory canal were orderly arranged, and no acne, papules, and pustules were found. After the right ear of the rabbits in the model control group was coated with coal tar, the ear became thicker and harder, and the surface was rough and dry. There was black keratotic plug at the hair follicle opening, forming blackhead acne, and the hair follicle opening was raised like a papule, which was rough, and part of it fused into one piece. In the right ear of the siPcsk9 treatment group, the skin of the ear was rough and thick, the papules were flatter than before, the hair follicle keratotic plugs were still visible, and the pores were slightly reduced. In the small molecule compound treatment group, the skin of the right ear of the rabbit was thinner than that of the left ear, most of the follicular papules subsided, the acne was reduced and flattened, the pores were reduced, and the skin was slightly dry. The right ear of the monoclonal antibody treatment group, the polypeptide treatment group, and the combined treatment group showed thin and soft skin, reduced acne, significantly reduced pores, no desquamation, and was close to the normal rabbit ear. Compared with the left ear, the right ear of the rabbits in the positive treatment group had mild redness, a little desquamation, and a small amount of hair follicle keratotic plugs and acne. No papules were found.

Tissue section observation: the left ear of the model group showed that the epidermis was thinner, hair follicles were visible, and the junction between the dermis and the epidermis was clear. After modeling of the right ear in the model group, the epidermis was thickened, hyperkeratosis was seen, the granular layer and the spinous layer were thickened, the hair follicles were enlarged, the keratotic plug blocked the opening of the hair follicle, and extended to the sebaceous gland. the hair follicle funnel was filled with keratinized substances and expanded into a pot shape; the capillaries in the upper dermis were dilated. Inflammatory cells scattered around the hair follicle and a small number of neutrophils were infiltrated; the number and volume of sebaceous glands both increased.

Histological grading of experimental acne under the microscope in each group (see Table 8): the right ears of rabbits in the model group were compared with their left ears (blank control), and the difference was statistically significant ($P<0.05$). The right ears of rabbits in each treatment group were compared with that of rabbits in the model group, and the difference was statistically significant ($P<0.05$). The thickness of the right ear epidermis, hair follicle volume and sebaceous gland diameter of the model group were compared with those of the left ear (blank control), and the differences were statistically significant ($P<0.05$), indicating that the rabbit ear acne model was successfully replicated; the skin thickness, hair follicle volume and sebaceous gland diameter of the right ears of rabbits in each treatment group were compared with those of rabbits in the model group, and the differences were statistically significant ($P<0.05$) (see Table 8)

TABLE 8

Histological grading of acne pimples in each group

| Group | n | Histological grading | | | |
|---|---|---|---|---|---|
| | | − | 1+ | 2+ | 3+ |
| Model group left ear | 10 | 10 | 0 | 0 | 0 |
| Model group right ear | 10 | 0 | 1 | 5 | 4 |
| Compound group1 | 10 | 6 | 3 | 1 | 0 |
| Compound group2 | 10 | 7 | 2 | 1 | 0 |
| Compound group3 | 10 | 5 | 3 | 2 | 0 |
| Compound group4 | 10 | 5 | 2 | 3 | 0 |
| Monoclonal antibody group1 | 10 | 8 | 2 | 0 | 0 |
| Monoclonal antibody group2 | 10 | 9 | 1 | 0 | 0 |
| Monoclonal antibody group3 | 10 | 9 | 1 | 0 | 0 |
| RNA interference group1 | 10 | 4 | 5 | 1 | 0 |
| RNA interference group2 | 10 | 6 | 3 | 1 | 0 |
| RNA interference group3 | 10 | 5 | 4 | 1 | 0 |
| Peptide group | 10 | 5 | 4 | 1 | 0 |
| Combination therapy group1 | 10 | 8 | 2 | 0 | 0 |
| Combination therapy group2 | 10 | 8 | 1 | 1 | 0 |
| Positive treatment group | 10 | 6 | 2 | 2 | 0 |

It can be seen from Table 8 that compound group 1-4, monoclonal antibody group 1-3, interfering RNA group 1-3, polypeptide group and combined treatment group with the effect of inhibiting PCSK9 have different degrees of improvement compared with the right ear of the model group. The effect of monoclonal antibody group 1-3 is better than that of other groups. Considering that the main reason is that the method of administration is injection, which belongs to internal administration, so the effect is better. Other groups are applied externally, and the effect will be reduced accordingly, However, it is also superior to the right ear of the model group, and at the same time, it is also equivalent to the treatment effect of the positive treatment group. Especially, the treatment effect of the combined treatment group has reached the level similar to that of the best effect of the monoclonal antibody group. Considering that the combined treatment group is applied externally, the administration method is easier than that of the monoclonal antibody group, the inventor believes that the combined treatment group will inevitably produce more excellent effect than the single use.

The skin thickness, hair follicle accumulation and sebaceous gland diameter of the right ear in the model group were compared with those in the left ear (blank control), and the difference was statistically significant ($P<0.05$), indicating that the rabbit ear acne model was successfully replicated; The skin thickness, hair follicle plot and sebaceous gland diameter of the right ear of rabbits in each treatment group were compared with those in the model group, and the difference was statistically significant ($P<0.05$) (see Table 9). The ear epidermis thickness, hair follicle area and sebaceous gland diameter of each group are shown in Table 9 below.

TABLE 9

Ear epidermis thickness, hair follicle area and sebaceous gland diameter in each group

| Group | n | Skin thickness (mm) | Hair follicle area ($mm^2$) | Sebaceous gland diameter (mm) |
|---|---|---|---|---|
| Left ear of model group | 10 | 0.1238 ± 0.0082* | 0.1052 ± 0.0978* | 0.0426 ± 0.0695* |
| Right ear of model group | 10 | 0.2913 ± 0.0242 | 0.4821 ± 0.1743 | 0.4127 ± 0.1436 |
| Compound group1 | 10 | 0.2433 ± 0.0196* | 0.2726 ± 0.0842* | 0.0512 ± 0.0327* |
| Compound group2 | 10 | 0.1968 ± 0.0121* | 0.2353 ± 0.0812* | 0.0467 ± 0.0313* |
| Compound group3 | 10 | 0.2245 ± 0.0185* | 0.2836 ± 0.0851* | 0.0542 ± 0.0346* |
| Compound group4 | 10 | 0.2276 ± 0.0193* | 0.2853 ± 0.0879* | 0.0561 ± 0.0362* |
| Monoclonal antibody treatment group 1 | 10 | 0.2325 ± 0.0189* | 0.2218 ± 0.0826* | 0.0465 ± 0.0312* |
| Monoclonal antibody treatment group 2 | 10 | 0.1532 ± 0.0156* | 0.1533 ± 0.0562* | 0.0432 ± 0.0267* |
| Monoclonal antibody treatment group 3 | 10 | 0.1547 ± 0.0149* | 0.1526 ± 0.0723* | 0.0435 ± 0.0285* |
| RNA interference group 1 | 10 | 0.2546 ± 0.0211* | 0.2954 ± 0.1065* | 0.0781 ± 0.0518* |
| RNA interference group2 | 10 | 0.1856 ± 0.0179* | 0.1836 ± 0.0856* | 0.0561 ± 0.0423* |
| RNA interference group3 | 10 | 0.1987 ± 0.0185* | 0.1921 ± 0.0933* | 0.0615 ± 0.0476* |
| Peptide group | 10 | 0.2362 ± 0.0192* | 0.2462 ± 0.1142* | 0.0532 ± 0.0415* |
| Combined treatment group1 | 10 | 0.1723 ± 0.0115* | 0.2046 ± 0.0782* | 0.0448 ± 0.0296* |
| Combined treatment group2 | 10 | 0.1851 ± 0.0118* | 0.2136 ± 0.0789* | 0.0463 ± 0.0302* |
| Positive treatment group | 10 | 0.2461 ± 0.0205* | 0.2915 ± 0.0867* | 0.0569 ± 0.0836* |

*Compared with the right ear of the model group, $P < 0.05$

It can be seen from Table 9 that compared with the left ear of the model group and the positive treatment group, the skin thickness, hair follicle area and sebaceous gland diameter of the right ear of the model group increased significantly, while the compound group 1-4, monoclonal antibody group 1-3, interfering RNA group 1-3, polypeptide group and the combined treatment group also increased slightly, but the increase was not significant. The data value of the monoclonal antibody treatment group 2-3 was basically the same as that of the left ear of the model group, Considering that the main reason is that the way of administration is injection, which belongs to internal administration, so the effect is better. Other groups are applied externally, and the effect will be reduced, but it is also better than the right ear of the model group. At the same time, it is also equivalent to the treatment effect of the positive treatment group, especially the combined treatment group, whose treatment effect has reached the level of 2-3 similar to that of the best monoclonal antibody treatment group, Considering that the combination treatment group is applied externally, and the method of administration is easier than that of the monoclonal antibody group, the inventor believes that the combination treatment group has also produced more excellent results than the single use.

3. Conclusion

PCSK9 small molecule compound inhibitors, PCSK9 RNA interference, PCSK9 monoclonal antibodies, and PCSK9 polypeptide inhibitors can significantly inhibit the symptoms of coal-tar-induced rabbit ears acne model, reduce pore blockage and blackheads formation, and are mild and non-irritating to the skin, indicating that it has therapeutic effect on acne.

Example 5 Effects of PCSK9 Gene Knockout on Androgenetic Alopecia (SA)

1. Methods 1.1 Animal Grouping and Modeling

Experimental animals: SPF grade C57BL/6 (B6) mice, C57BL/6-PCSK9−/− mice (using CRISPR gene editing technology to knock out the Pcsk9 gene exon 2-3 to establish a Pcsk9 gene knockout mouse model).

Mice with different genotypes were divided into three groups: C57BL/6 mouse negative control group, C57BL/6 mouse model group, and C57BL/6-PCSK9−/− mouse model group, with 6 mice in each group, 3 males and 3 females. The back of each mouse was depilated as an observation area. Except for the negative control group, mice in other groups were injected with testosterone propionate injection [8 ml/(kg·d)] subcutaneously at the back of the neck, once a day for 60 days to establish the SA model. After continuous subcutaneous injection of testosterone propionate for 30 days, hair loss gradually appeared in mice, which proved that the androgenetic alopecia model was successfully established.

1.2 Observation Indexes and Test Methods

Every 10 days, 10 hairs were extracted from the observation area on the back of each mouse, and the length of the hair was measured with a vernier caliper. At the end of the experiment, the skin of the experimental observation area was taken for routine tissue dehydration, paraffin embedding, staining, and light microscope examination to observe the histopathological changes of mouse skin hair follicles and sebaceous glands, and the expression of vascular endothelial growth factor (VEGF) protein in the skin of each group was detected by immunohistochemistry. Semi-quantitative analysis was carried out for each group. The grading standards were as follows: normal skin dermal tissue cells, subcutaneous hair follicles, and sebaceous glands were marked as "one": no hyperplasia was found in the skin and dermis, hair follicles and sebaceous glands were limited, and no inflammation was marked as "±": no obvious hyperplasia was found in the dermis, and follicles were obviously cystic. No obvious hyperplasia was found in the sebaceous glands, and no inflammation was marked as "+": segmental hyperplasia of skin and dermis found in the dermis was not obvious, a small number of hair follicles had cystic degeneration, and sebaceous glands had mild hyperplasia and hypertrophy. No obvious inflammation under the skin was recorded as "++": the skin dermis tissue cells had segmental hyperplasia of different levels, showing uneven hair follicle size and no cells in the periphery, and some hair follicles had cystic degeneration. There was hyperplasia of sebaceous glands and few nuclei in the hyperplasia glands. Individual mice have mild inflammatory hyperplasia under the skin, which is marked as "+++".

2. Results 2.1 Effects on Mouse Hair Growth

The hair length of the C57BL/6-PCSK9−/− mouse model group was longer than that of the C57BL/6 (B6) mouse model group on the 10th, 20th, and 30th days of modeling, and the differences were statistically significant (P<0.01). See Table 10. The hair growth of mice in each group on the 30th day of modeling is shown in Table 10

TABLE 10

Hair growth length of mice in each group

| Group | 10 days hair length (mm) | 20 days hair length (mm) | 30 days hair length (mm) |
|---|---|---|---|
| Negative control group | 3.42 ± 0.41 | 5.32 ± 0.52 | 6.83 ± 0.59* |
| C57BL/6mouse model group | 2.61 ± 0.36 | 3.06 ± 0.41 | 3.92 ± 0.45 |
| C57BL/6-PCSK9-/-mouse model group | 3.03 ± 0.38 | 4.96 ± 0.43* | 6.26 ± 0.51* |

*To compare with C57BL/6 (B6) mouse model group (P < 0.01)

2.2 Effect on the Morphology of the Superficial Dermis Hair Follicles in the Skin Tissue of the Mouse Observation Area In the C57BL/6 (B6) mouse model group, some dermal cells were segmentally thickened at different levels, and there was slight lymphocyte proliferation under the skin; some mice had obvious cystic degeneration in the subcutaneous hair follicles, hair follicles were different in size, and there was mild peripheral Fibrosis. Cells around the hair follicle disappeared or the cell layer was significantly reduced, the number of sebaceous glands was increased, some glands were hypertrophic, the nuclei of the hypertrophic glands were significantly reduced, and the number of normal hair follicles was reduced. Compared with the C57BL/6 mouse model group, the skin dermal tissue cells, subcutaneous hair follicles, and sebaceous gland lesions of the C57BL/6-PCSK9−/− mouse model group were decreased to varying degrees, and the number of skin-damaged hair follicles was significantly reduced, and the difference was statistically significant (P<0.01), see Table 11 Immunohistochemical results showed that the expression of VEGF protein in the skin hair follicles of the model group was decreased. Compared with the model group, the expression of VEGF protein in the PCSK9−/− mouse model group was higher and compared with the negative control group, there was no significant difference, as shown in Table 11.

TABLE 11

Effects of each group on skin hair follicles and sebaceous glands of mice (only)

| Group | — | ± | + | ++ | +++ | P value |
|---|---|---|---|---|---|---|
| Negative control group | 6 | 0 | 0 | 0 | 0 | <0.01 |
| C57BL/6 mouse model group | 0 | 0 | 1 | 1 | 4 | — |
| C57BL/6-PCSK9-/-mouse model group | 0 | 3 | 2 | 1 | 0 | <0.01 |

*To compare with C57BL/6 (B6) mouse model group (P < 0.01)

3. Conclusion

PCSK9 gene knockout can increase the expression of VEGF in skin hair follicle tissues, significantly promote the hair growth of mice with androgenetic alopecia, and reduce the damage to the subcutaneous hair follicles and sebaceous glands.

Example 6 Effects of PCSK9 Inhibitors on Hair Growth in Mice

1. Method 1.1 Materials (1) PCSK9 RNA-1 interference sequence and modification are shown in table 12.

TABLE 12

| Genes | 5'-3' Sense | 5'-3' Antisense |
|---|---|---|
| siPCSK9-1 | GccuGGAGuuuAuucGGAAdT*dT | UUCCgAAuAAACUCcAGGCdT*dT |
| siPCSK9-2 | AGGuGuAucuccuAGAcAcdT*dT | GUGUCuAGGAGAuAcACCUdT*dT |

Mix equal amounts of siPcsk9-1 and 2 and dilute them to 20 μM with normal saline, and mix the diluted siRNA evenly with the lotion. PCSK9 RNAi inhibitor-2: RNA sequence is the same as Alnylam's Inclisran; PCSK9RNAi inhibitor-3: RNA sequence is the same as Affiris' ALN-PCS.

(2) PCSK9 small molecule compound inhibitor 1: R-IMPP from Selleck, chemical formula: C24H27N3O2, molecular weight: 389.49, structural formula:

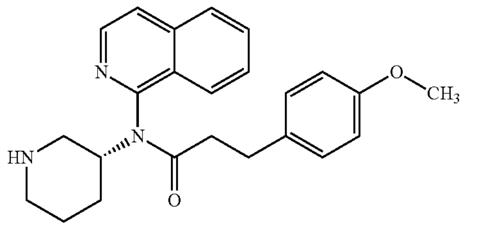 [SMILES: COc1ccc(CCC(=O)N(c2nccc3ccccc23)[C@@H]2CCCNC2)cc1]

PCSK9 small molecule compound inhibitor 2: PF 06446846 from Selleck, chemical formula: C22H20ClN7O, molecular weight: 434.04, structural formula:

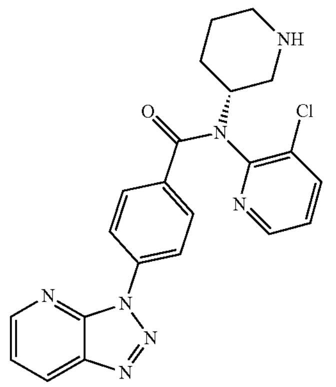 [SMILES: O=C(c1ccc(-n2nnc3cccnc32)cc1)N(c1ncccc1Cl)[C@@H]1CCCNC1]

PCSK9 small molecule compound inhibitor 3: Selleck company product SBC-115076, chemical formula: C31H33N3O5, molecular weight: 527.61, structural formula:

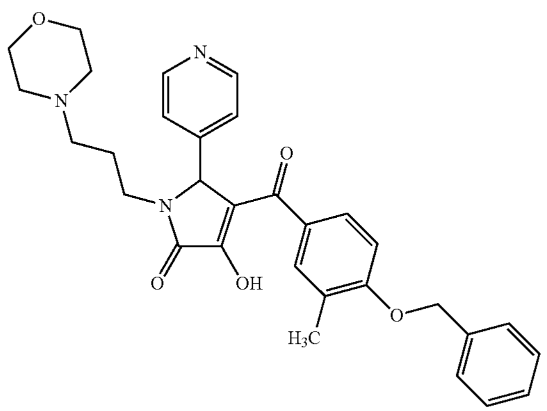 [SMILES: Cc1cc(C(=O)C2=C(O)C(=O)N(CCCN3CCOCC3)C2c2ccncc2)ccc1OCc1ccccc1]

PCSK9 small molecule compound inhibitor 4: Selleck company product SBC-110736, chemical formula: C26H27N3O2, molecular weight: 413.51, structural formula:

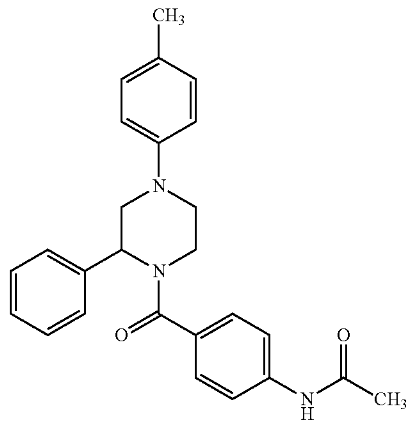 [SMILES: CC(=O)Nc1ccc(C(=O)N2CCN(c3ccc(C)cc3)CC2c2ccccc2)cc1]

(3) PCSK9 monoclonal antibody 1: purchased from Abcam company (ab84041); PCSK9 monoclonal antibody 2: Evolocumab; PCSK9 monoclonal antibody 3: Alirocumab.

(4) PCSK9 polypeptide-11 is ab32727 of Abcam Company.

Preparation method of treatment solution: 60% ethanol is mixed with an appropriate amount of PCSK9 inhibitor to prepare solutions of different concentrations.

1.2 Animal Grouping and Modeling

SPF grade C57BL/6 mice were selected and numbered according to their weight. They were randomly divided into compound group 1 (skin applied with 2% R-IMPP solution), compound group 2 (skin applied with 2% PF 06446846 solution), and compound group 3 (skin applied with 2% SBC-115076 solution), compound group 4 (skin applied with 2% SBC-110736 solution), monoclonal antibody group 1 (PCSK9subcutaneous injection monoclonal antibody ab81041, 5 mg/kg·d), monoclonal antibody group 2 (Subcutaneous injection of Evolocumab, 5 mg/kg·d), monoclonal antibody group 3 (subcutaneous injection of Alirocumab, 5 mg/kg·d), PCSK9 RNA interference group-1 (skin applied with 2% PCSK9 small interfering RNA-1 solution), PCSK9 RNA interference Group-2 (skin applied with 2% PCSK9 small interfering RNA-2 solution), PCSK9 RNA interference group-3 (skin applied with 2% PCSK9 small interfering RNA-3 solution), polypeptide group (subcutaneous injection of Abcam company ab32727, 3 mg/kg·d), positive control group (skin applied with 2% minoxidil solution), negative control group (skin applied with 60% ethanol), and model control group (skin applied with 60% ethanol), 10 mice in each group, half male and half female. After the mice were anesthetized with ether, they were coated on the back with a mixture of rosin and paraffin (1:1) after hot melting, and then peeled off after it solidified and hardened. The back of the mouse was cleaned to be hairless and without injuries. The depilation area was about 3 cm×4 cm. From the 2nd day after depilation, the corresponding drugs were applied to the hair removal area, twice a day, 0.5 mL per animal each time, and subcutaneously injected once a week.

1.3 Observation Indicators and Methods 1.3.1 Visual Observation

From the second day after application, observe the daily color change of the skin on the back of the mice to determine the growth state of the hair follicles and visually observe the hair growth in the depilation area, and score the new hair growth in the depilation area once a day. Five mice in each group were reserved for 40 days of visual observation, and the growth of back hair was recorded.

1.3.2 Histological Observation

On the 17th day, five mice in each group were sacrificed by cervical dislocation. The samples were taken from the same part of the back parallel to the spine, fixed with 10% formaldehyde, dehydrated, embedded in paraffin, sectioned, stained with HE, and sealed with neutral gum. Then the histology of hair follicles was observed under light microscope, and morphological staging of hair follicles was performed. According to the international hair cycle scoring method, the hair follicles were scored as follows: 100 points for growth stage VI, 200 points for early regression, 300 points for middle regression, and 400 points for late regression. 50 hair follicles were randomly selected from each mouse, the cycle of the hair follicles in each group was determined, and the average hair cycle score and the percentage of hair follicles in the growth phase VI, early regression, middle regression, and late regression were calculated.

1.4 Statistical Methods:

The experimental data were statistically processed with SPSS 16.0 system software. The statistical variables of experimental data are expressed in (x±s), using x2 test and t test, α The value is taken from both sides, P>0.05 indicates no significant difference, P<0.05 indicates significant difference, and P<0.01 indicates significant difference.

2. Results 2.1 Visual Observation of Changes in the Hair Plucking Site of Mice

After hair plucking in C57BL/6 mice, a highly synchronized new hair cycle can be induced in the modeling area, that is, although the hair removal part is still pink on the first to fifth days after hair removal, the hair follicle has shown histologically the growth of stage I to III; the skin color turns black on the 7th day, and the hair follicle had entered the growth stage IV histologically; The hair follicles in the hair removal area were in the growth stage VI from the 9th to the 10th day. After 18 days, the local skin turned grayish-black, and the histological hair follicles had changed in the degenerative stage. On the 20th day after the plucking, the plucked hairs turned pink again, and the histological hair follicles entered a resting stage.

In this experiment, the back skin of the mice in the negative control group and the model control group changed from pink to black on the 7th day after hair removal, and then it changed from black to grayish-black on the 17th day after plucking. In contrast, the back skin of the mice in the inhibitor group and the positive control group changed from pink to black on the 6th day after hair plucking, and the color of the back skin changed from black to gray-black on the 20th day after hair removal. The specific change time is shown in Table 13. It can be seen that there is no significant difference in the skin color, grayish-black time, and black duration in the hair-plucking area of the mice in each inhibitor group compared with the positive control group (all P>0.05). Compared with the negative control group and the model control group, there were extremely significant differences (P<0.01). It was suggested that PCSK9 inhibitors can obviously prolong the growth period of hair follicles.

TABLE 13

Time of skin color change in the hair removal area on the back of mice in each group (days)

| Group | Skin black-turning time | Skin grayish-black-turning time | Black skin duration |
|---|---|---|---|
| Model control group | 7.26 | 17.27 | 10.01 |
| Negative control | 7.09* | 17.56 | 10.47 |
| Positive control group | 6.29* | 19.09* | 12.80 |
| Compound group 1 | 5.96* | 20.25* | 14.29* |
| Compound group 2 | 5.45* | 17.32* | 10.86* |
| Compound group 3 | 5.63* | 18.12* | 11.65* |
| Compound group 4 | 5.78* | 18.46* | 12.32* |
| Monoclonal antibody group 1 | 6.20* | 19.26* | 13.06* |
| Monoclonal antibody group 2 | 5.23* | 16.83* | 10.21* |
| Monoclonal antibody group 3 | 5.35* | 16.65* | 13.43* |
| RNA interference group 1 | 6.23* | 19.21* | 12.98* |
| RNA interference group2 | 5.66* | 18.23* | 11.87* |
| RNA interference group3 | 6.08* | 18.52* | 12.16* |
| Peptide group | 6.13* | 19.38 | 13.25* |

Note:
*Compared with the negative control group and the model control group, P < 0.01.

2.2 Hair Growth in the Hair Removal Area on the Back of Mice

The negative control group and the model control group showed that new hair appeared in the hair removal area on the back on the 11th day after plucking, and the hair length in the hair removal area on the 37th day was consistent with that in the non-experimental area. In the inhibitor group and the positive control group, new hair appeared in the back plucked area on the 7th day, and the hair removal area hair was the same length as the non-experimental area on the 19th day. The specific hair growth time is shown in Table 14. It can be seen that there was no significant difference in the growth rate of new hair between the mice in the inhibitor group and the positive control group (all P>0.05), and there was a significant difference between the inhibitor group, the negative control group, and the model control group (P<0.01). It was suggested that the inhibitor has an obvious effect on promoting hair growth.

TABLE 14

Hair growth time of back hair removal area of mice in each group (days)

| Group | Time to grow new hair | Time to match the length of hair in the non-experimental area | Time from hair growth to the same length as the hair in the non-experimental area |
|---|---|---|---|
| Model control group | 11.36 | 38.26 | 26.90 |
| Negative control | 11.12 | 37.01 | 26.89 |
| Positive control group | 7.85 | 23.62 | 15.77 |
| Compound Group1 | 6.92* | 18.06* | 11.14* |
| Compound Group2 | 6.33* | 17.69* | 10.46* |
| Compound Group3 | 6.95* | 19.35* | 11.52* |

TABLE 14-continued

| Hair growth time of back hair removal area of mice in each group (days) | | | |
|---|---|---|---|
| Group | Time to grow new hair | Time to match the length of hair in the non-experimental area | Time from hair growth to the same length as the hair in the non-experimental area |
| Compound Group4 | 6.98* | 18.46* | 11.87* |
| Monoclonal antibody group1 | 6.34* | 18.65* | 12.31* |
| Monoclonal antibody group2 | 5.78* | 16.68* | 9.89* |
| Monoclonal antibody group3 | 6.06* | 16.75* | 10.13* |
| RNA interference group 1 | 7.06* | 21.61* | 14.55* |
| RNA interference group 2 | 6.92* | 20.16* | 14.12* |
| RNA interference group 3 | 6.96* | 21.38* | 14.26* |
| Peptide group | 6.81* | 20.75* | 13.94* |

Note:
*Compared with the negative control group and the model control group, there are significant differences (P < 0.01)

2.3 Immunohistochemistry of Hair Follicles

On the 17th day after hair removal, it can be seen that the base of the hair follicle in the negative control group and the model control group became thinner and lighter in color, the lower part of the hair follicle degenerated, the dermal papilla became round and dense, the epithelial cord between the dermal papilla and the blastocyst was formed, the inner hair root sheath partially disappeared, and the hairs have rod-shaped ends. However, the hair follicles in the PCSK9 inhibitor group and the positive control group were larger and longer, and most of the hair follicles were still in the VI stage of growth and in the early stage of regression. On the 17th day after hair plucking, the average hair cycle scores of the PCSK9 inhibitor group (McAb group, polypeptide group, compound group, siPcsk9 group) and positive control group were 158, 167, 165, 168, 172, and 185, respectively, indicating the growth of hair follicles in stage VI and early stage of degeneration. The average hair cycle scores of the negative control group and the model control group were 306 points and 345 points, respectively, which corresponded to the middle and late stages of hair follicle degeneration. The percentages of hair follicles in the growth stage VI of the inhibitor group (McAb group, polypeptide group, compound group, siPcsk9 group), positive control group, negative control group, and model control group were 56%, 52%, 53%, 47%, 47%, 42%, 13%, and 11%respectively. There were significant differences between the inhibitor group and the model control group in the percentage of growth stage VI hair follicles (P<0.01); there was no significant difference between the inhibitor group and the positive control group in the percentage of hair follicles in the growth phase VI (P>0.05). It was suggested that PCSK9 inhibitors can significantly prolong the growth period of hair follicles and promote hair growth.

Example 7 Effects of Various PCSK9 Inhibitors on Androgenetic Alopecia (SA) Rat Model 1. Method 1.1 Materials (1) PCSK9 RNA-1 interference sequence and modification are shown in table 15.

TABLE 15

| Genes | 5'-3' Sense | 5'-3' Antisense |
|---|---|---|
| siPCSK9-1 | GccuGGAGuuuAuucGGAAdT*dT | UUCCgAAuAAACUCcAGGCdT*dT |
| siPCSK9-2 | AGGuGuAucuccuAGAcAcdT*dT | GUGUCuAGGAGAuAcACCUdT*dT |

PCSK9 RNAi inhibitor-2: RNA sequence is the same as Alnylam's Inclisran; PCSK9RNAi inhibitor-3: RNA sequence is the same as Affiris' ALN-PCS.

(2) PCSK9 small molecule compound inhibitor 1: R-IMPP from Selleck, chemical formula: C24H27N3O2, molecular weight: 389.49, structural formula:

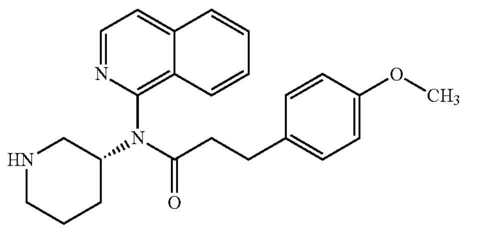 [SMILES: COc1ccc(CCC(=O)N(c2nccc3ccccc23)[C@@H]2CCCNC2)cc1]

PCSK9 small molecule compound inhibitor 2: PF 06446846 from Selleck, chemical formula: C22H20ClN7O, molecular weight: 434.04, structural formula:

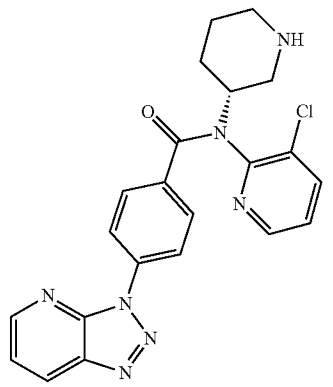 [SMILES: O=C(c1ccc(-n2nnc3cccnc32)cc1)N(c1ncccc1Cl)[C@@H]1CCCNC1]

PCSK9 small molecule compound inhibitor 3: Selleck company product SBC-115076, chemical formula: C31H33N3O5, molecular weight: 527.61, structural formula:

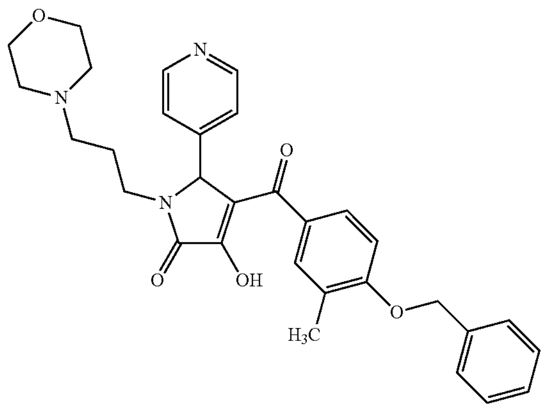 [SMILES: Cc1cc(C(=O)C2=C(O)C(=O)N(CCCN3CCOCC3)C2c2ccncc2)ccc1OCc1ccccc1]

PCSK9 small molecule compound inhibitor 4: Selleck company product SBC-110736, chemical formula: C26H27N3O2, molecular weight: 413.51, structural formula:

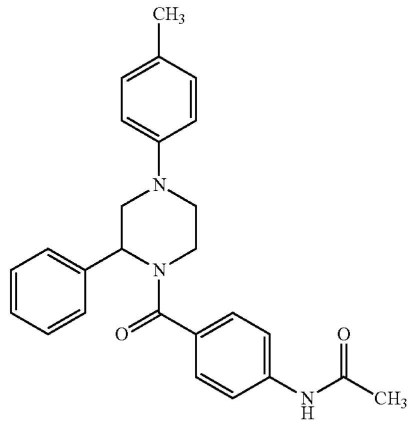 [SMILES: CC(=O)Nc1ccc(C(=O)N2CCN(c3ccc(C)cc3)CC2c2ccccc2)cc1]

(3) PCSK9 monoclonal antibody 1: purchased from Abcam company (ab84041); PCSK9 monoclonal antibody 2: Evolocumab; PCSK9 monoclonal antibody 3: Alirocumab.

(4) PCSK9 series polypeptide inhibitors were synthesized by Shanghai Shenggong. The amino acid sequence of PCSK9 polypeptide-1 is EYPYKHSGYYHRP; The amino acid sequence of PCSK9 polypeptide-2 is: EYTFKHSGYYHRP; The amino acid sequence of PCSK9 polypeptide-3 is EYPWKGSGYYHRP; The amino acid sequence of PCSK9 polypeptide-4 is: EYTYNGAGYYHRP; and PCSK9 polypeptide 11 is ab32727 of Abcam Company.

Preparation method of treatment solution: 75% ethanol is mixed with an appropriate amount of PCSK9 inhibitor to prepare solutions of different concentrations.

1.2 Animal Grouping and Modeling

SPF grade Wistar rats were selected and randomly divided into compound group 1 (skin applied with 5% R-IMPP solution), compound group 2 (skin applied with 5% PF 06446846 solution), and compound group 3 (skin applied with 5% SBC-115076 solution), compound group 4 (skin applied with 5% SBC-110736 solution), monoclonal antibody group 1 (subcutaneous injection of PCSK9 monoclonal antibody ab84041, 5 mg/kg·d), monoclonal antibody group 2 (subcutaneous injection of Evolocumab, 5 mg/kg·d), monoclonal antibody group 3 (subcutaneous injection of Alirocumab, 5 mg/kg·d), PCSK9 RNAi inhibitor group-1 (skin applied with 5% PCSK9 small interfering RNA-1 solution), PCSK9 RNAi inhibitor group-2 (skin applied with 5% PCSK9 small interfering RNA-2 solution), PCSK9 RNAi inhibitor group-3 (skin applied with 5% PCSK9 small interfering RNA-3 solution), and polypeptide group (subcutaneous injection of Abcam company ab32727, 3 mg/kg·d), positive control group (skin smeared with 5% minoxidil tincture), negative control group (smeared with 75% ethanol), model control group (smeared with 75% ethanol), 10 rats in each group, half male and half female.

Before the experiment, each rat selected an area of 4 cm×5 cm on the back to remove the hair as the observation area. Except for the negative control group, the rats were subcutaneously injected with testosterone propionate injection [5 ml/(kg·d)] at the back of the neck, once a day for 60 consecutive days to establish the SA model. After 4 weeks of continuous subcutaneous injection of testosterone propionate, the rats gradually appeared hair loss, and the remaining hair became thin and brittle, which proved that the androgenetic alopecia model was successfully established. At the same time, the rats in the corresponding drug group were smeared or subcutaneously injected on the skin of the observation area of the rats in the drug group, smeared 1 ml/(per time), twice a day, with an interval of 8 hours, and administered by subcutaneous injection, once a day. The negative control group and the model control group were smeared with excipient (75% ethanol solution), 1 mL one rat per time, twice a day, for 60 consecutive days.

1.3 Observation Indexes and Methods 10 hairs were extracted from the observation area on the back of each rat every 15 days after administration, and the hair length was measured with a vernier caliper. After 60 days of administration, the skin of the experimental observation area was taken for routine tissue dehydration, paraffin embedding, HE staining, and light microscopy to observe the histopathological changes of the rat skin hair follicles and sebaceous glands. Semi-quantitative analysis was carried out in each group. The grading standards are as follows: normal skin dermal tissue cells, subcutaneous hair follicles, and sebaceous glands were marked as "one"; no hyperplasia in the dermis, limited lesions of hair follicles and sebaceous glands, and no subcutaneous inflammation, marked as "±"; no obvious hyperplasia found in the dermis, obviously cystic follicles, no obvious hyperplasia found in the sebaceous glands, and no inflammation is recorded as "+"; segmental hyperplasia of skin and dermis was not obvious, a small number of hair follicles had cystic degeneration, and sebaceous glands had mild hyperplasia and hypertrophy. No obvious inflammation under the skin was recorded as "++"; the skin and dermis tissue cells had segmental hyperplasia of different degrees, some follicles degenerated, the size of the hair follicles was uneven, and there were no cells in the periphery. There was hyperplasia of sebaceous glands, and there were few nuclei in the hyperplasia glands. Individual rats had mild inflammatory hyperplasia under the skin, which was marked as "+++".

2. Results 2.1 Effects on Rat Hair Growth

The hair length of the rats in the PCSK9 inhibitor group was longer than that in the model control group on the 15th, 30th, 45th, and 60th days after the administration, and the differences were statistically significant ($P<0.01$). See Table 16

TABLE 16

Effects of each group on hair growth length of rats

| Group | 15 d hair length (mm) | 30 d hair length (mm) | 45 d hair length (mm) | 60 d hair length (mm) |
|---|---|---|---|---|
| Negative control group | 9.6 | 10.3 | 13.2 | 15.3 |
| Model group | 6.5 | 7.6 | 9.8 | 11.9 |
| Positive control group | 7.9* | 8.4* | 12.8* | 14.9* |
| Compound group 1 | 8.9* | 9.9* | 14.7* | 18.2* |
| Compound group 2 | 9.2* | 10.1* | 15.2* | 18.9* |
| Compound group 3 | 8.3* | 8.8* | 14.5* | 17.6* |
| Compound group 4 | 8.1* | 8.6* | 14.3* | 17.3* |
| Monoclonal antibody group 1 | 8.5* | 9.6* | 15.3* | 17.8* |
| Monoclonal antibody group 2 | 9.7* | 10.8* | 15.8* | 19.5* |
| Monoclonal antibody group 3 | 9.5* | 10.5* | 15.5* | 19.2* |
| RNAi group 1 | 7.9* | 8.8* | 13.2* | 16.5* |
| RNAi group 2 | 8.3* | 9.1* | 14.5* | 16.9* |
| RNAi group 3 | 8.2* | 8.9* | 14.2* | 16.7* |
| Peptide group | 8.2* | 9.3* | 14.1* | 17.6* |

*Compared with the model control group, the difference was statistically significant ($P < 0.01$)

2.2 Influence on the Morphology of Hair Follicles in the Superficial Dermis of the Skin Tissue in the Observation Area of the Rats In the model group, some skin and dermal tissue cells of the rats have different degrees of segmental thickening, and the rats had mild lymphocyte hyperplasia under the skin; some rats had obvious cystic changes in the subcutaneous hair follicles, the size of the hair follicles varied, and there were exfoliated horns in the enlarged hair follicle cavity. There was mild fibrosis around the hair follicle, the cells around the hair follicle disappear or the cell layer was significantly reduced, the cavity seemed to have calcifications stained blue, the number of sebaceous glands increased, some glands were hypertrophic, the nuclei of the hypertrophic glands were significantly reduced, and the number of normal hair follicles was reduced. Compared with the model group, the lesions of skin dermal tissue cells, subcutaneous hair follicles, and sebaceous glands of the rats in the PCSK9 inhibitor group and the minoxidil tincture group were alleviated to different degrees. Compared with the model control group, the number of damaged hair follicles in the PCSK9 inhibitor group was significantly reduced, and the difference was statistically significant (P<0.01). Compared with the model control group, the lesions of skin dermal tissue cells, subcutaneous hair follicles, and sebaceous glands of the rats in the PCSK9 inhibitor group and the minoxidil tincture group were significantly reduced, and the difference was statistically significant (P<0.01). See Table 17.

TABLE 17

Effects of each group on rat skin hair follicles and sebaceous glands

| Group | Number | — | ± | + | ++ | +++ | Pvalue * |
|---|---|---|---|---|---|---|---|
| Negative control group | 10 | 10 | 0 | 0 | 0 | 0 | <0.01 |
| Model control group | 10 | 0 | 0 | 2 | 3 | 5 | — |
| Positive control group | 10 | 0 | 3 | 5 | 2 | 0 | <0.01 |
| Compound group 1 | 10 | 0 | 5 | 2 | 3 | 0 | <0.01 |
| Compound group 2 | 10 | 2 | 5 | 2 | 1 | 0 | <0.01 |
| Compound group 3 | 10 | 1 | 4 | 2 | 3 | 0 | <0.01 |
| Compound group 4 | 10 | 1 | 4 | 3 | 2 | 0 | <0.01 |
| Monoclonal antibody group1 | 10 | 0 | 5 | 3 | 2 | 0 | <0.01 |
| Monoclonal antibody group2 | 10 | 3 | 4 | 3 | 0 | 0 | <0.01 |
| Monoclonal antibody group3 | 10 | 3 | 4 | 2 | 1 | 0 | <0.01 |
| RNAi group 1 | 10 | 0 | 3 | 4 | 3 | 0 | <0.01 |
| RNAi group 2 | 10 | 1 | 4 | 4 | 1 | 0 | <0.01 |
| RNAi group 3 | 10 | 1 | 3 | 4 | 2 | 0 | <0.01 |
| Peptide group | 10 | 0 | 3 | 3 | 4 | 0 | <0.01 |

Note:
* means there is a statistically significant difference compared with the model control group (P < 0.01)

Example 8 Effects of PSCK9 Gene Knockout on Rat Scar (Scar) Model

1. Methods 1.1 Grouping and modeling of experimental animals: SPF rats, PCSK9−/− SPF rats (using CRISPR gene editing technology to knock out Pcsk9 gene exon 2-3 to obtain Pcsk9 gene knockout rats), body weight (220±26) g, male. They were divided into model control group and PCSK9−/− group, with 6 rats in each group. Rats in each group were anesthetized by intraperitoneal injection of 2% pentobarbital sodium (120 mg/kg) and then fixed on the operating table, and then a 4×5 cm piece of intact skin was selected on the left side of the back, and 8% sodium sulfide was used for dehairing. Tissue scissors were used to cut a 2.4 cm diameter round wound deep into the muscle fascia at the depilation site, and part of the muscle surface fascia was destroyed. To prevent rats from biting and licking, the animals were kept in separate cages. The wounds were routinely disinfected with 2% iodine tincture daily, and the wound healing of the rats was observed. On the 20th day, the rats were anesthetized with 2% sodium pentobarbital, and about 0.5 cm*0.5 cm of the wound skin edge tissue was collected for the fibroblast culture and subsequent experiments.

1.2 Fibroblast culture and identification

Take the wound tissue and make it into a size of 1 mm*1 mm, inoculate it in a culture dish, and add 0.5 ml of DMEM medium.

1.3 TUNEL Kit to Detect In Situ Apoptosis

TUNEL is a method to detect apoptotic DNA fragmentation, which is widely used to identify and quantify apoptotic cells, or to detect excessive DNA fragmentation in a single cell. This assay relies on the use of terminal deoxynucleotidyl transferase (TdT), which is an enzyme that catalyzes the attachment of deoxynucleotides labeled with fluorescent dyes or another label to the 3'-hydroxyl end of DNA double-strand breaks, and it can also label DNA with damaged cells in other ways. The concentration of the cell suspension used in the experiment was adjusted to $1\times10^5$/ml with MEM and inoculated into 100 ml culture flasks, 10 ml per flask. The cells were cultured at 37° C. under the conditions of 5% CO2 and 95% humidity, and the cultured cells were pipetted into a cell solution after 24 h, 48 h, and 72 h, respectively, and the cells were collected. They were centrifuged at 2500 rpm for 5 min, the supernatant was removed, and 1 ml of 75% ethanol was added to each bottle for fixation. Staining was performed as required by the TUNEL Apoptosis Assay Kit, and expression in the mean distribution of apoptotic fibroblast units in all fields was manually calculated with a manual counter for statistical comparison.

1.4 MTT Assay to Detect Cell Proliferation

MTT chemical name 3-(4,5-dimethylthiazole-2)-2,5-diphenyltetrazolium bromide, trade name thiazole blue. Detection principle: The succinate dehydrogenase in the mitochondria of living cells can reduce exogenous MTT to water-insoluble blue-purple crystalline formazan (Formazan), which was deposited in cells, while dead cells had no such function. Dimethyl sulfoxide (DMSO) can dissolve formazan in cells, and its light absorption value was measured by enzyme-linked immunosorbent assay, which can indirectly reflect the number of living cells. The amount of MTT crystals formed in a certain range of cell numbers was proportional to the cell number. The cells were seeded in a 48-well culture plate at a density of $1.0\times10^5$/ml, and cultured in a 100 µl, 37° C., 5% CO2 incubator until the cells adhered. After culturing for 24 h, 48 h, and 72 h in the incubator, 20 µl of MTT (5 mg/ml) was added to each well for 4 hours, the medium was aspirated, 100 µl of DMSO lysate was added, and cells were incubated at a 37° C., 5% CO2 incubator for 20 min. After the purple crystals were completely dissolved, the absorbance (optical density value) was measured on a microplate reader at 570 nm. The proliferation of fibroblasts in each group was compared.

1.4 Statistical Methods:

SPSS 16.0 statistical software was used for data analysis. The measurement data are expressed as mean±standard deviation (x±s), and compared by one-way ANOVA. The data of the two groups are compared by t-test. $P<0.05$ is statistically significant, and $P<0.01$ is statistically significant.

2. Results 2.1 Observation Results of Rat Wounds

The wounds were routinely disinfected every day, and the wounds of rats were observed on the 1st, 3rd, 5th, 7th, 12th, and 20th day. From the third day of the observation period, the wound recovery speed of the PCSK9−/− group was significantly faster than that of the model group, and the wound area became smaller. On the 12th day, the wounds in the PCSK9−/− group had basically recovered, leaving only a small amount of scabs, while the model group still had wounds about 0.5 cm2 in size. On the 20th day, the wounds in both groups had basically recovered. The model control group samples had scars, while the PCSK9−/− group ones had less pigmentation and no obvious scars.

2.2 TUNEL Assay to Detect Fibroblast Apoptosis

TUNEL is a method to detect the fragmentation of apoptotic DNA and is widely used to identify and quantify apoptotic cells. The results showed that the apoptosis index of fibroblasts in PCSK9−/− group and model control group were 16.816±1.012 and 2.151±0.563, respectively, and the apoptosis index of fibroblasts in PCSK9−/− group was significantly higher than that in the model control group ($P<0.01$).

2.3 MTT Assay to Detect Fibroblast Proliferation

Dimethyl sulfoxide (DMSO) can dissolve formazan in cells, and its light absorption value was measured at a wavelength of 490 nm with an enzyme-linked immunosorbent assay, which can indirectly reflect the number of living cells. Within a certain range of cells, the amount of MTT crystal formation was proportional to the number of cells. The results showed that the average absorbance values of PCSK9 −/− group and model control group were 0.31 and 0.52 respectively after 24 h of culture, 0.26 and 0.57 after 48 h of culture, and 0.21 and 0.66 after 72 h of culture. Compared with the model control group, the absorbance value of PCSK9−/− group began to decrease significantly after culturing for 24 h, and the absorbance value of PCSK9−/− group decreased more obviously after culturing for 72 h, and the difference was more obvious compared with the model control group. The experimental results showed that PCSK9 knockout could significantly reduce the proliferation activity of fibroblasts.

3. Conclusions

Knockout of PSCK9 gene can significantly promote skin wound healing, reduce fibroblast proliferation activity, promote fibroblast apoptosis, and reduce scar (scar) formation. It showed that knockout of PSCK9 gene has preventive and therapeutic effects on scar.

Example 9 Effects of Various PSCK9 Inhibitors on Rat Scar Model

1. Method 1.1 Materials (1) PCSK9 RNA-1 interference sequence and modification are shown in table 18.

TABLE 18

| Genes | 5'-3' Sense | 5'-3' Antisense |
|---|---|---|
| siPCSK9-1 | GccuGGAGuuuAuucGGAAdT*dT | UUCCgAAuAAACUCcAGGCdT*dT |
| siPCSK9-2 | AGGuGuAucuccuAGAcAcdT*dT | GUGUCuAGGAGAuAcACCUdT*dT |

Mix equal amounts of siPcsk9-1 and 2 and dilute them to 20 μM with normal saline, and mix the diluted siRNA evenly with the lotion.

PCSK9 RNAi inhibitor-2: RNA sequence is the same as Alnylam's Inclisran; PCSK9RNAi inhibitor-3: RNA sequence is the same as Affiris' ALN-PCS.

(2) PCSK9 small molecule compound inhibitor 1: R-IMPP from Selleck, chemical formula: C24H27N3O2, molecular weight: 389.49, structural formula:

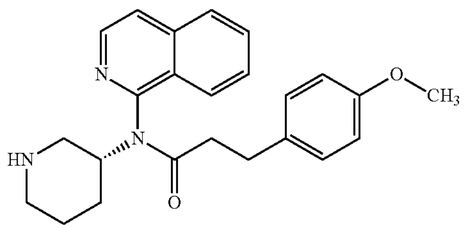 [SMILES: COc1ccc(CCC(=O)N(c2nccc3ccccc23)[C@@H]2CCCNC2)cc1]

PCSK9 small molecule compound inhibitor 2: PF 06446846 from Selleck, chemical formula: C22H20ClN7O, molecular weight: 434.04, structural formula:

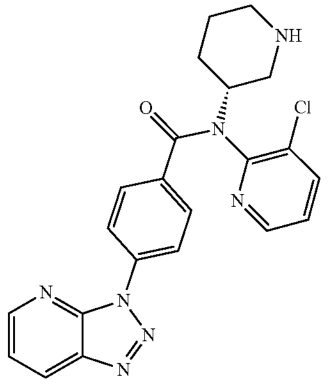 [SMILES: O=C(c1ccc(-n2nnc3cccnc32)cc1)N(c1ncccc1Cl)[C@@H]1CCCNC1]

PCSK9 small molecule compound inhibitor 3: Selleck company product SBC-115076, chemical formula: C31H33N3O5, molecular weight: 527.61, structural formula:

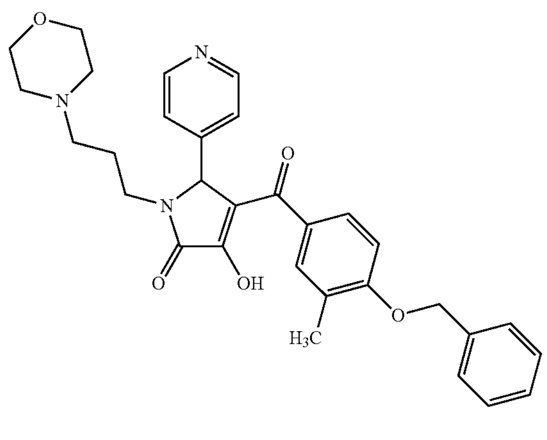 [SMILES: Cc1cc(C(=O)C2=C(O)C(=O)N(CCCN3CCOCC3)C2c2ccncc2)ccc1OCc1ccccc1]

PCSK9 small molecule compound inhibitor 4: Selleck company product SBC-110736, chemical formula: C26H27N3O2, molecular weight: 413.51, structural formula:

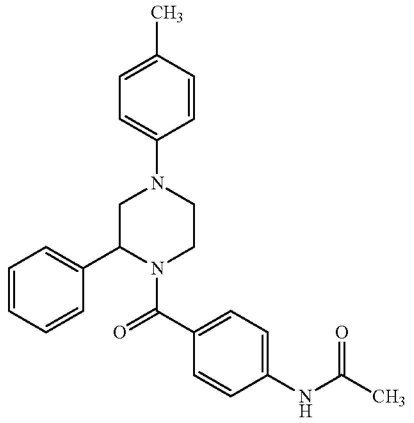 [SMILES: CC(=O)Nc1ccc(C(=O)N2CCN(c3ccc(C)cc3)CC2c2ccccc2)cc1]

(3) PCSK9 monoclonal antibody 1: purchased from Abcam company (ab84041); PCSK9 monoclonal antibody 2: Evolocumab; PCSK9 monoclonal antibody 3: Alirocumab.

(4) the amino acid sequence of PCSK9 polypeptide-9 is ab32727 of Abcam Company. Schering-Plough China Co., Ltd.)

(5) Positive therapeutic drug: mometasone furoate cream (trade name: aloxone, produced by Schering-Plough China Co., Ltd.)

(6) Experimental animals: SPF black guinea pigs, weighing (252±18) g, half male and half female.

(7) Preparation method of therapeutic cream: The excipient matrix components include methyl silicone oil (15%), stearic acid (6%), white vaseline (5%), liquid paraffin (5%), octadecanol (5%), glycerin (20%), alkyl aryl polyglycol ether (1%), fatty alcohol polyoxyethylene ether (1%), tween-807 (1%), ethyl paraben (0.1%), distilled water (about 31-55%), and mixed with more than appropriate amount of PCSK9 inhibitors to form a mixed emulsion. The cream matrix used in this embodiment refers to the matrix component from which the active ingredient is removed from the cream.

1.2 Grouping and modeling of experimental animals: SPF male rats, weighing (210±28) g, were obtained from the Animal Center of Southern Medical University. Rats were numbered by body weight and randomly divided into compound group 1 (skin applied with 0.5% R-IMPP cream), compound group 2 (skin applied with 0.5% PF 06446846 cream), compound group 3 (skin applied with 0.5% PF 06446846 cream), and compound group 4 (skin application of 0.5% SBC-110736 cream), monoclonal antibody group 1 (subcutaneous injection of PCSK9 monoclonal antibody ab84041, 3 mg/kg·d), monoclonal antibody group 2 (subcutaneous injection of Evolocumab, 3 mg/kg·d), monoclonal antibody group 3 (subcutaneous injection of Alirocumab, 3 mg/kg·d), PCSK9 RNA interferencegroup-1 (skin smeared with 0.5% PCSK9 small interfering RNA-1 cream), PCSK9 RNA interference group-2 (skin smeared with 0.5% PCSK9 small interfering RNA-2 cream), PCSK9 RNA interference group-3 (skin smeared with 0.5% PCSK9 small interfering RNA-3 cream), polypeptide group (ab32727 of Abcam company subcutaneously injected, 3 mg/kg·d), positive treatment group (skin smeared with Eloson), blank control group (skin smeared with Vaseline), model group (with tail vein injection of normal saline), 6 rats in each group, each group was administered twice a day, subcutaneous injection every day 1 time. Rats in each group were anesthetized by intraperitoneal injection of 2% pentobarbital sodium (120 mg/kg) and then fixed on the operating table, and then a 4×5 cm piece of intact skin was selected on the left side of the back, and dehaired with 8% sodium sulfide. A 2.4 cm diameter round wound was cut by tissue scissors to the muscle surface at the depilation site to destroy part of the muscle surface fascia Animals were kept in separate cages to prevent rats from biting and licking. The wounds were routinely disinfected with 2% iodine tincture daily, and the wound healing of the rats was observed.

2. Results 2.1 Observation Results of Rat Wounds

The wounds were routinely disinfected every day, and the wounds of rats were observed on the 1st, 3rd, 5th, 7th, 12th, and 20th day. From the 5th day, the wound recovery speed of the small molecule compound treatment group, PCSK9 small interfering RNA treatment group, PCSK9 monoclonal antibody treatment group, and positive treatment group was significantly faster than that of the model group, and the wound area gradually decreased. The wound recovery rate of PCSK9 polypeptide inhibitor treatment group was better than that of the model group and the blank control group from the 7th day. On the 12th day, the wounds in the small molecule compound treatment group, the PCSK9 small interfering RNA treatment group, and the PCSK9 monoclonal antibody had basically recovered, while the model group and the blank control group still had wounds of about 0.4 cm2 and 0.36 cm2 in size, respectively. The polypeptide inhibitor treatment group still had wounds about 0.2 cm2 in size. On the 20th day, the wounds in each group had recovered, and the model control group and the blank control group left obvious scars, while the other groups only left varying amounts of pigmentation.

3. Conclusion

PCSK9 inhibitors can significantly promote skin wound healing and reduce scar formation.

Example 10 Effects of PSCK9 gene knockout on rat pulmonary fibrosis model

1. Method 1.1 Materials:

(1) Reagents: bleomycin (4 mg/piece, Tianjin Taihe Pharmaceutical Co., Ltd.), mouse anti-mouse MMP monoclonal antibody (NEO Mark-ers company), mouse anti-mouse TIMP-1 polyclonal antibody (Wuhan Boster company), enzyme-linked immunosorbent assay (ELISA) kit (American R & D company), Quantscript RT Kit reverse transcription kit (Dalian TaKaRa company).

(2) Experimental animals SPF Wistar rats, PCSK9−/− SPF Wistar rats (using CRISPR gene editing technology to knock out Pcsk9 gene exon 2-3 to obtain Pcsk9 gene knockout rats), body weight (181±22) g, male.

1.2 Animal Grouping and Modeling

Rats were numbered by body weight and divided into blank control group, model group, and PCSK9−/− group by random arrangement method, with 6 rats in each group. Rats in each group were anesthetized by intraperitoneal injection of 2% sodium pentobarbital (120 mg/kg), fixed on the operating table, and injected into the neck trachea. The blank control group was injected with normal saline (1.25 ml/kg), and the model group and PCSK9−/− group were injected with 5 U/mL bleomycin solution (5 mg/kg), once a day for 14 consecutive days.

1.3 Observation Indexes and Test Methods

Peripheral venous blood was collected from the tail vein 14 days after modeling, and the levels of superoxide dismutase (SOD) and catalase (CAT) in peripheral blood were detected. The rats in each group were sacrificed after blood collection, and the right lung tissue of the animals was collected and stored at −4° C. for the detection of VEGF. The left lung tissue was routinely embedded in paraffin and sectioned, and the MMP subtypes and TIMP-1 expression in rat lung tissue were detected by immunohistochemical staining. When detecting VEGF, the right lung tissue was taken out for grinding and tissue homogenization, high-speed centrifugated at 3000 r/min, and the supernatant was collected to detect VEGF protein in lung tissue by ELISA. The expression of VEGF-mRNA by reverse transcription polymerase chain method was applied.

1.4 Statistical Methods

Data analysis was performed using SPSS 16.0 statistical software. Measurement data were expressed as mean±standard deviation (x±s), one-way analysis of variance was used for comparison, t test was used for pairwise comparison, and P<0.05 was considered statistically significant.

2. Results 2.1 The Effect of PSCK9 Gene Knockout on MMP in Rat Lung Tissue

There was a little expression of TIMP-1 and MMP isoforms in the lung tissue of rats in the blank control group. The expressions of MMP-2 and MMP-9 in the model group increased after modeling, while TIMP-1 decreased, and the difference was statistically significant compared with the blank control group (P<0.05), indicating that the modeling was successful. The expressions of MMP-2 and MMP-9 in the PCSK9−/− group were lowered, and the expression of TIMP-1 was up-regulated, and the difference was statistically significant compared with the model group (P<0.05). See Table 19

TABLE 19

Comparison of TIMP-1 and MMP expressions in lung tissues of rats in each group (n = 6, x ± s)

| Group | TIMP-1 | MMP-2 | MMP-9 |
|---|---|---|---|
| Model control group | 5.71 ± 0.63 | 3.86 ± 0.29 | 5.17 ± 0.39 |
| Blank control group | 8.95 ± 0.56* | 2.41 ± 0.18* | 3.29 ± 0.22* |
| PCSK9-/-group | 8.87 ± 0.58* | 2.43 ± 0.21* | 3.32 ± 0.23* |

Note:
*Compared with the model control group, P < 0.05.

2.2 The Effect of PSCK9 Gene Knockout on VEGF in Lung Tissue

The expressions of VEGF protein and VEGF-mRNA in lung tissue of rats in each group are shown in Table 20. The expression of VEGF protein and VEGF-mRNA in the model group was significantly lowered, and the difference was statistically significant compared with the blank control group (P<0.05), indicating that the pulmonary fibrosis model was successfully established. There were significant differences in the expression of VEGF protein and VEGF-mRNA between the PCSK9−/− group and the model group (P<0.05).

TABLE 20

Comparison of VEGF protein and VEGF-mRNA expression levels in lung tissues of each group (n = 6, x ± s)

| Group | VEGF protein (pg/ml) | VEGF-mRNA |
|---|---|---|
| Model control group | 37.23 ± 4.16 | 0.52 ± 0.19 |
| Blank control group | 54.26 ± 3.95* | 0.83 ± 0.13* |
| PCSK9-/-group | 56.12 ± 3.67* | 0.85 ± 0.15* |

Note:
*Compared with the model control group, P < 0.05.

2.3 Effects of PSCK9 Gene Knockout on SOD and CAT Enzyme Activities in Peripheral Blood The levels of SOD and CAT enzymes in peripheral blood of rats in each group are shown in Table 21. The peripheral blood SOD and CAT enzyme activities of the rats in the model group were decreased, and the difference was statistically significant compared with that of the blank control group (P<0.05). The activity of SOD and CAT enzyme in peripheral blood of rats in PCSK9 −/− group was increased, and the differences compared with the model group were statistically significant (P<0.05).

TABLE 21

Comparison of SOD and CAT enzyme levels in peripheral blood of each group (n = 6, x ± s)

| Group | SOD (U/ml) | CAT (kU/g) |
|---|---|---|
| Model control group | 143.36 ± 15.23 | 8.87 ± 1.21 |
| Blank control group | 223.65 ± 13.28* | 15.16 ± 1.29* |
| PCSK9-/-group | 221.76 ± 13.57* | 14.98 ± 1.32* |

Note:
*Compared with the model control group, P < 0.05.

3. Conclusions

Knockout of PSCK9 gene can significantly reduce the levels of MMP-2 and MMP-9 in the lung tissue of the pulmonary fibrosis rat model, increase the levels of TIMP-1 and VEGF, and increase the levels of SOD and CAT enzymes in peripheral blood, indicating that it has an inhibitory effect on pulmonary fibrosis.

Example 11 Effects of PSCK9 Inhibitors on Pulmonary Fibrosis Rat Model

1. Methods 1.1 Materials:

(1) Reagents: bleomycin (4 mg/piece, Tianjin Taihe Pharmaceutical Co., Ltd.), mouse anti-mouse MMP monoclonal antibody (NEO Mark-ers company), mouse anti-mouse TIMP-1 polyclonal antibody (Wuhan Boster company), enzyme-linked immunosorbent assay (ELISA) kit (American R & D company), Quantscript RT Kit reverse transcription kit (Dalian TaKaRa company).

(2) siRNA sequence and modification are shown in table 22.

TABLE 22

| Genes | 5'-3' Sense | 5'-3' Antisense |
|---|---|---|
| siPCSK9-1 | GccuGGAGuuuAuucGGAAdT*dT | UUCCgAAuAAACUCcAGGCdT*dT |
| siPCSK9-2 | AGGuGuAucuccuAGAcAcdT*dT | GUGUCuAGGAGAuAcACCUdT*dT |

(3) PCSK9 small molecule compound inhibitor (Selleck company product R-IMPP), chemical formula: C24H27N3O2, molecular weight: 389.49

(4) PCSK9 monoclonal antibody was purchased from Abcam (ab84041)

(5) PCSK9 polypeptide was purchased from Abcam (ab32727)

(6) Experimental animals: SPF Wistar rats, half male and half female, aged 51-55 days, weighing (180±21) g, from the Animal Center of Nanjing Medical University.

1.2 Animal Grouping and Modeling

Rats were numbered according to their body weight and divided into groups according to their body weight by random arrangement table method, and divided into small molecule compound treatment group (tail vein injection of PCSK9 small molecule compound inhibitor, 3 mg/kg·d), siPcsk9 treatment group (Tail vein injection of PCSK9 small interfering RNA, 3 mg/kg·d), monoclonal antibody treatment group (tail vein injection of PCSK9 monoclonal antibody, 3 mg/kg·d), peptide treatment group (tail vein injection of PCSK9 polypeptide inhibitor, 3 mg/kg·d), model group (injection of physiological saline into tail vein, 3 mg/kg·d), and blank control group (injection of physiological saline into tail vein, 3 mg/kg·d), 12 animals in each group, half male and half female. Rats in each group were anesthetized by intraperitoneal injection of 2% sodium pentobarbital (120 mg/kg), fixed on the operating table, and injected into the neck trachea. The control group was injected with normal saline (1.25 ml/kg), and the model group and each treatment group were injected with 5 U/mL bleomycin solution (5 mg/kg). Starting from one week after modeling, each treatment group was injected with corresponding tail vein injection PCSK9 inhibitor solution, blank control group and model group were injected with equal volumes of normal saline through tail vein, once a day for 14 consecutive days 1.3 Observation Indexes and Test Methods Peripheral venous blood was collected from the tail vein of animals in each group after modeling and 14 days after treatment, and the levels of superoxide dismutase (SOD) and catalase (CAT) in peripheral blood were detected. Rats in each group were sacrificed twice after blood collection (after modeling and 14 days after treatment, 6 in each group), and the right lung tissue of the animals was stored in a −4° C. refrigerator for the detection of VEGF. The left lung tissue was routinely embedded in paraffin, sectioned, and immunohistochemical staining was used to observe the expression of MMP isoforms and TIMP-1 in rat lung tissue. When detecting VEGF, the right lung tissue was taken out for grinding, tissue homogenization, high-speed centrifugation at 3000 r/min, and the supernatant was collected to detect VEGF protein in lung tissue by ELISA. The expression of VEGF-mRNA by reverse transcription polymerase chain method was applied.

1.4 Statistical Methods

SPSS 16.0 statistical software was used for data analysis. The measurement data is expressed as mean±standard deviation (x±s). The comparison is made by one-way analysis of variance, and the comparison between the two is made by t-test. P<0.05 is statistically significant.

2. Experimental Results 2.1 Effects of PCSK9 inhibitors on MMP in rat lung tissue TIMP-1 and MMP subtypes were expressed in small amounts in the lung tissue of rats in the blank control group, and there was little change after modeling and 14 days of treatment. The expressions of MMP-2 and MMP-9 in the model group were increased after modeling and 14 days of treatment, while TIMP-1 was decreased, and the difference was statistically significant compared with the blank control group (P<0.05). As shown in Table 23, after 14 days of treatment, the expressions of MMP-2 and MMP-9 in each PCSK9 inhibitor group were decreased, and the expression of TIMP-1 was up-regulated, with a statistically significant difference compared with the model group (P<0.05).

TABLE 23

Comparison of the expression of TIMP-1 and MMP in the lung tissue of rats in each group (n = 6, x ± s)

| Group | TIMP-1 | MMP-2 | MMP-9 |
|---|---|---|---|
| Model group | 5.53 ± 0.72 | 3.91 ± 0.36 | 5.21 ± 0.32 |
| Blank control group | 8.96 ± 0.48* | 2.42 ± 0.21* | 3.29 ± 0.21* |
| Compound group | 8.56 ± 0.58* | 2.67 ± 0.32* | 3.43 ± 0.34* |
| siPcsk9treatment group | 8.24 ± 0.45* | 2.98 ± 0.26* | 3.56 ± 0.25* |
| Monoclonal antibody treatment group | 7.87 ± 0.51* | 3.24 ± 0.28* | 3.64 ± 0.27* |
| Peptide treatment group | 7.53 ± 0.54* | 3.05 ± 0.31* | 3.71 ± 0.23* |

Note:
*Compared with the model control group, P < 0.05.

2.2 Effects of PCSK9 Inhibitors on VEGF in Lung Tissue

The expressions of VEGF protein and VEGF-mRNA in lung tissue of rats in each group are shown in Table 24. After modeling and treatment for 14 days, the expression of VEGF protein and VEGF-mRNA in the lung tissue of the rats in the blank control group had no significant changes (P>0.05); The expression of VEGF protein and VEGF mRNA in the model group was significantly lower than that in the blank control group, which showed statistical significance (P<0.05). After 14 days of treatment, the expressions of VEGF protein and VEGF-mRNA in each PCSK9 inhibitor group were enhanced compared with those after modeling, and the differences were statistically significant compared with the model group (P<0.05).

TABLE 24

Comparison of VEGF protein and VEGF-mRNA expression levels in lung tissue of each group (n = 6, x ± s)

| | VEGF protein (pg/ml) | | VEGF-mRNA | |
|---|---|---|---|---|
| Group | 14 days after modeling | 14 days after treatment | 14 days after modeling | 14 days after treatment |
| Model group | 39.58 ± 3.71 | 38.65 ± 3.23 | 0.56 ± 0.17 | 0.53 ± 0.18 |
| Blank control group | 53.32 ± 3.09 | 52.46 ± 3.19* | 0.76 ± 0.08 | 0.83 ± 0.13* |
| Compound group | 38.47 ± 3.23 | 57.61 ± 3.86* | 0.53 ± 0.16 | 0.85 ± 0.16* |

TABLE 24-continued

Comparison of VEGF protein and VEGF-mRNA expression levels in lung tissue of each group (n = 6, x ± s)

| Group | VEGF protein (pg/ml) | | VEGF-mRNA | |
|---|---|---|---|---|
| | 14 days after modeling | 14 days after treatment | 14 days after modeling | 14 days after treatment |
| siPcsk9 treatment group | 39.43 ± 3.18 | 54.23 ± 3.43* | 0.59 ± 0.15 | 0.82 ± 0.14* |
| Monoclonal antibody treatment group | 38.96 ± 3.22 | 52.78 ± 3.61* | 0.56 ± 0.16 | 0.79 ± 0.19* |
| Peptide treatment group | 39.05 ± 3.26 | 52.12 ± 3.58* | 0.54 ± 0.17 | 0.77 ± 0.16* |

Note:
*Compared with the model control group, P < 0.05.

2.3 Effects of PCSK9 Inhibitors on SOD and CAT Enzyme Activities in Peripheral Blood The levels of SOD and CAT enzymes in the peripheral blood of rats in each group are shown in Table 25. After modeling and treatment for 14 days, the peripheral blood SOD and CAT enzyme activities of the rats in the blank control group had no significant changes (P>0.05). The peripheral blood SOD and CAT enzyme activities of the rats in the model group were decreased, and the difference was statistically significant compared with the blank control group (P<0.05). After 14 days of treatment, the peripheral blood SOD and CAT enzyme activities of the rats in each PCSK9 inhibitor group were enhanced compared with the model group, the difference was statistically significant (P<0.05).

TABLE 25

Comparison of SOD and CAT enzyme levels in peripheral blood of each group (n = 6, x ± s)

| Group | SOD (U/ml) | | CAT (kU/g) | |
|---|---|---|---|---|
| | 14 days after modeling | 14 days after treatment | 14 days after modeling | 14 days after treatment |
| Model group | 172.97 ± 14.72 | 145.76 ± 15.49 | 9.46 ± 2.19 | 8.96 ± 1.42 |
| Blank control group | 218.98 ± 13.29 | 221.87 ± 13.08* | 15.73 ± 1.95 | 15.12 ± 0.92* |
| Compound group | 171.45 ± 13.92 | 218.56 ± 14.36* | 9.43 ± 2.31 | 14.45 ± 1.51* |
| siPcsk9 treatment group | 172.13 ± 14.58 | 214.65 ± 13.92* | 9.45 ± 1.97 | 14.06 ± 1.43* |
| Monoclonal antibody treatment group | 172.85 ± 14.81 | 215.13 ± 13.64* | 9.47 ± 1.85 | 13.36 ± 1.45* |
| Peptide treatment group | 173.21 ± 14.45 | 212.67 ± 14.62* | 9.39 ± 2.23 | 13.23 ± 1.52* |

Note:
*Compared with the model control group, P < 0.05.

3. Conclusions

PCSK9 inhibitors can significantly reduce the levels of MMP-2 and MMP-9 in the lung tissue of the pulmonary fibrosis rat model, and increase the levels of TIMP-1 and VEGF; at the same time, all of them can increase the levels of SOD and CAT enzymes in the peripheral blood, indicating that it has therapeutic effect on pulmonary fibrosis.

Finally, it should be noted that the above embodiments are only used to illustrate the technical solution of the invention, not to limit it; Although the present invention has been described in detail with reference to the preceding embodiments, ordinary technical personnel in the art should understand that they can still modify the technical solutions recorded in the preceding embodiments, or replace some or all of the technical features equally; However, these modifications or replacements do not make the essence of the corresponding technical solutions separate from the scope of the technical solutions of the embodiments of the invention.

The invention claimed is:

1. A method of treating alopecia by administration of a therapeutically effective amount of a PCSK9 inhibitor to a human in need thereof, wherein the PCSK9 is a pro-protein convertase Bacillus subtilis invertase/kexin9 type, belonging to the pro-protein convertase family, wherein the PCSK9 inhibitor includes a PCSK9 small molecule compound inhibitor, and the PCSK9 small molecule compound inhibitor includes the compound as shown by formula II, or a pharmaceutically acceptable salt thereof, Formula II

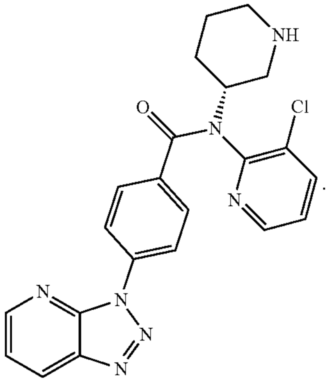

2. The method of claim 1, wherein the PCSK9 inhibitor is administered alone or in combination with other therapeutic drugs for treating alopecia.

3. The method of claim 1, wherein the alopecia is alopecia areata, androgenetic alopecia, or antineoplastic drug-caused alopecia.

4. The method of claim 1, wherein the compound is administered topically.

5. The method of claim 4, wherein the compound is formulated as a cream or solution comprising the compound in a concentration of 2% to 5%.

6. The method of claim 1, wherein the alopecia is androgenetic alopecia.

7. The method of claim 1, wherein the compound promotes hair growth, or reduces damage to hair follicles and sebaceous glands.

* * * * *